United States Patent
Ben-Sasson et al.

(10) Patent No.: US 7,115,707 B2
(45) Date of Patent: Oct. 3, 2006

(54) AMINO ACID SEQUENCES CAPABLE OF FACILITATING PENETRATION ACROSS A BIOLOGICAL BARRIER

(75) Inventors: Shmuel A. Ben-Sasson, Jerusalem (IL); Einat Cohen, Jerusalem (IL)

(73) Assignee: Chiasma, Inc., NY (US)

( * ) Notice: Subject to any disclaimer, the term of this patent is extended or adjusted under 35 U.S.C. 154(b) by 14 days.

(21) Appl. No.: 10/665,184

(22) Filed: Sep. 17, 2003

(65) Prior Publication Data

US 2004/0146549 A1    Jul. 29, 2004

Related U.S. Application Data

(63) Continuation-in-part of application No. PCT/IB03/00968, filed on Feb. 7, 2003.

(60) Provisional application No. 60/355,396, filed on Feb. 7, 2002.

(51) Int. Cl.
*A61K 38/00* (2006.01)
*C07K 1/00* (2006.01)

(52) U.S. Cl. .................. 530/300; 530/350; 514/12

(58) Field of Classification Search ............... 530/350, 530/300; 514/12
See application file for complete search history.

(56) References Cited

U.S. PATENT DOCUMENTS

| | | | |
|---|---|---|---|
| 4,179,337 A * | 12/1979 | Davis et al. | 435/181 |
| 4,873,316 A | 10/1989 | Meade et al. | |
| 2003/0060438 A1 * | 3/2003 | Henry et al. | 514/44 |
| 2004/0176476 A1 * | 9/2004 | Gyurik | 514/772.6 |

FOREIGN PATENT DOCUMENTS

| WO | WO 96/05858 | 2/1996 |
|---|---|---|
| WO | WO 03/066859 A2 | 8/2003 |

OTHER PUBLICATIONS

Henry et al., U.S. Appl. No. 60/226,086, filed Aug. 18, 2000.*
Gyurik, U.S. Appl. No. 60/300,293, filed Jun. 22, 2001.*
Ho et al., Influence of pluronic F-68 on dissolution and bioavailability characteristics of multiple-layer pellets of nifedipine for controlled release delivery, Journal of controlled release, vol. 68, issue 3, Sep. 3, 2000, pp. 433-440.*
Written Opinion for PCT/IB03/00968, mailing date: Jul. 8, 2004.
Amann, et al., *Gene*, 69(2):301-315 (1988).
Armstrong, W.M., *Physiol. Gastrointest. Tract*, 2$^{nd}$ Ed., Johnson, ed., Raven Press, New York, 2:1251-1265 (1987).
Baldari, et al., *EMBO J.*, 6(1):229-234 (1987).
Banerji, et al., *Cell*, 729-740 (1983).
Bernkop-Schnurch, et al., *J. Control. Release*, 52:1-16 (1998).
Byrne, et al., *Proc. Natl. Acad. Sci. USA*, 86:5473-5477 (1989).
Calame, et al., *Adv. Immunol.*, 43:235-275 (1988).
Camper, et al., *Genes Dev.*, 3(4):537-546 (1989).
Edlund, et al., *Science*, 230:912-916 (1985).
Fox, *Curr. Opin. Pharmacol.*, 2:338-344 (2002).
Gottesman, *Gene Expression Technology: Methods in Enzymology 185*, Academic Press, San Diego, Calif., pp. 119-128 (1990).
Gumbiner, *Am. J. Physiol.*, 253(6):C749-C758 (1987).
Inoue, et al., *Inflamm. Res.*, 45(7):316-323 (1996).
Jackson, L.R., *Physiol. Gastrointest. Tract*, 2$^{nd}$ Ed., Johnson, ed., Raven Press, New York, 2:1597-1621 (1987).
Kaufman, et al., EMBO J., 6:187-195 (1987).
Kessel, et al., *Science*, 249:374-379 (1990).
Kurjan, et al., *Cell*, 30(3):933-943 (1982).
Luckow, et al., *Virology*, 170(1):31-39 (1989).
Madara, *J. Clin. Invest.*, 83(4):1089-1094 (1989).
Merrifield, R.B., *J. Am. Chem. Soc.*, 85:2151-2154 (1963).
O'Shaughnessy, et al., *Euro. J. Pharm.*, 236(2):319-321 (1993).
Pinkert, et al., *Genes Dev.*, 1(3):268-277 (1987).
Queen, et al., *Cell*, 33:741-748 (1983).
Schilfgaarde, et al., *Infect. Immun.*, 68(8):4616-4623 (2000).
Schultz, et al., *Gene*, 54(1):113-123 (1987).
Seed B., *Nature*, 329:840-842 (1987).
Smith, et al., *Mol. Cell. Biol.*, 3(12):2156-2165 (1983).
Studier, et al., *Gene Expression Technology: Methods in Enzymology*, Academic Press, San Diego, Calif., 185:60-89 (1990).
Wada, et al., *Nucl. Acids Res.*, 20:2111-2118 (1992).
Weintraub, et al., "Anti-sense RNA as a Molecular Tool for Genetic Analysis", *Reviews-Trends in Genetics*, 1:22-25 (1985).
Winoto, et al., *EMBO J.*, 8(3):729-733 (1989).
Yowell, et al., *Cancer Treat. Rev.*, 28(Suppl. A):3-6 (2002).

* cited by examiner

*Primary Examiner*—Jon Weber
*Assistant Examiner*—Robert B. Mondesi
(74) *Attorney, Agent, or Firm*—Mintz, Levin, Cohn, Ferris, Glovsky and Popeo, P.C.; Ivor R. Elrifi, Esq.; Christina K. Stock, Esq.

(57) ABSTRACT

This invention relates to novel pharmaceutical penetration compositions capable of facilitating penetration of at least one effector across biological barriers. The invention also relates to methods of treating or preventing diseases by administering penetration compositions to affected subjects.

40 Claims, 4 Drawing Sheets

Figure 1

Amino Acid Sequence Alignment of ORF HI0638

```
Haemophilus Influenzae HI0638   -MKNYHD-IVLALAGVCQSAKLVHQLATESRADSETFLTALNSLFITQPQ
Pasteurella multocida           -MANYYD-ITLALAGVCQAAKLVQQFAHEGQADQAAFETSLNTLLQIYPE
Escherichia coli                MAKNYYD-ITLALAGICQSARLVQQLAHQGHCDADALHVSLNSIIDMNPS
Vibrio cholerae                 MANAIYD-RTIAFAGICQAVALVQQVAKNGYCDSDAFETSLKAITCTNPS
Buchnera aphidicola             -MKKIHL-ITLSLAGICQSAHLVQQLAYSGKCDSNAFSICLKSILEINPT
Pseudomonas aeruginosa          -MSDPRQ-QLIALGAVFESAALVDKLARTGQISEAPLGCMLGSLLARNPA
Xylella fastidiosa              -MNALIDNRVLALAGVVQALQQVRQIAETGQSETSAVRTAINSVLRIDAE
                                         :        :         ::               .

RIEDVFGGEVRHLKLGLETLIHQLNAQGD----QNLTRYWLSLLALEGKLSKNSDAKQTLGNRISRLKEQEIHYARDSE-TMLSIMANIYSDIIS
DTLAVFGGKAQNLKIGLETLLEQMHGTG-----SDLSRYWISLLALESKLNKDPHAKAELARRIQYLPTQLEHYDLLDE-QMLSTLASIYVDVIS
STLAVFGGSEANLRVGLETLLGVLNASSRQGLNAELTRYTLSLMVLERKLSSAKGALDTLGNRINGLQRQLEHFDLQSE-TLMSAMAAIYVDVIS
NTLEVFG-HESQLKLGLECLVKGIDSTPS--G-SEITRYLISLMALERKLSGRRDAMSQLGDRIQMIERQLDHFDLFDD-QMISNLASIYLDVIS
SFIAIYGNHEKNLIIGLEILLSTLTFSSFSYSYIELIKYISNMMIIEKKLKKSRTAIYSLKNKISVIS-SEYYLNYNIK-NLTRKLGELYLEIIS
STLDVYGGDSLNLRDGFKALASALERKPGS-LQREPLRYALAMLTLERQLDKRGDMLDLIGQRLDQVEQQVQHFGLVHE-NVIASFASIYQDTLS
SPEAVYG-RIRDLTQGLQLLHDYFGNQLR---DQLLPRLALAVLQLERRFIRDTSIVAAVSAGITQAAHQVEQTGDSAHPEVLSTLGALYANTIS
  .  *  .*  **: *                ::  ::  ::     *  :: .*    .   .        .     ::  :: .:*  :*

PLGKKIHILGSPDYLRQELVQNKIRAVLLAGIRSAVLWKQMGGTKWQILFFRRKLLATAKQIYSSIY---    SEQ ID NO:59
PLGKKIQVTGSTLYLQQLAMHHRIRACLLAGIRSAVLWRQVGGTKWQVLFSRRKIIAMAKQIYSSL----    SEQ ID NO:60
PLGPRIQVTGSPAVLQSPQVQAKVRATLLAGIRAAVLWHQVGGGRLQLMFSRNRLTTQAKQILAHLTPEL   SEQ ID NO:61
PIGPRIQVTGTPAVLQQTANQHKVRALLLSGIRCAVLWRQVGGRRRHLIFGRKKMIEQAQILLAR-----   SEQ ID NO:62
SLGSRIVIKGIKDFLQDHQIQEKIRCLLFSGIRAIVLWKQYGGNQLQLIYFRYFIKKAKKILYHLKDAT    SEQ ID NO:63
TFRQRIQVHGDMRHLQVSSNAARIRALLAGIRSARLWRQLGGSRWQMVFSRRRLLNELYPLLRG------   SEQ ID NO:64
HLRPRIIVQGNPHYLGQAGVVAEIRAMLLAALRSAVLWRQLNGNLLDFMLAKRAMAAATERALR------   SEQ ID NO:65
   . :*  *      .:*. *:::*.  ***.*   .  .  :
```

Figure 2

Homology Search of the N-terminus (amino acids 3-26)

| | | | |
|---|---|---|---|
| Haemophilus influenzae | N Y H D I V L A L A G V C Q S A K L V H Q L A | SEQ ID NO:1 |
| Pasteurella multocida | N Y Y D I T L A L A G V C Q Q A A K L V Q F A | SEQ ID NO:2 |
| Escherichia coli | N Y Y D I T L A L A G I C Q Q S A R L V Q L A | SEQ ID NO:3 |
| Vibrio cholerae | A I Y D R T I A F A G I C Q Q A V A L V Q V A | SEQ ID NO:4 |
| Buchnera aphidicola | K I H L I T L S L A G I C Q Q S A H L V Q L A | SEQ ID NO:5 |
| Pseudomonas aeruginosa | D P R Q Q L I A L G A V F E S A A L V D K L A | SEQ ID NO:6 |
| Xylella fastidiosa | L I D N R V L A L A G V V Q A L Q Q V R Q I A | SEQ ID NO:7 |
| Rhizobium loti (prot1) | N L P P I V L A V I G I C A A V F L L Q Q Y V | SEQ ID NO:8 |
| Human NK-2 RECEPTOR | N Y F I V N L A L A D L C M A A F N A A F N F | SEQ ID NO:9 |
| Chlamydia pneumoniae | T A F D F N K M L D D G V C T Y V V K G V Q Y L | SEQ ID NO:10 |
| Rhizobium loti (prot2) | R A I L I P L A L A G L C Q V A R A G D I S S | SEQ ID NO:11 |
| NprB Bac. Subtilis | M R N L T K T S L L L A G L C T A A Q M V F V T H | SEQ ID NO:12 |

Glucose Levels in Mice Following Insulin Translocation Across Epithelial Cell Membranes Glucose Levels in Rats Following Insulin Translocation Across Epithelial Cell Membranes

SEQUENCE LISTING

<160> NUMBER OF SEQ ID NOS: 65

<210> SEQ ID NO 1
<211> LENGTH: 23
<212> TYPE: PRT
<213> ORGANISM: haemophilus influenzae

<400> SEQUENCE: 1

Asn Tyr His Asp Ile Val Leu Ala Leu Ala Gly Val Cys Gln Ser Ala
1               5                   10                  15

Lys Leu Val His Gln Leu Ala
            20

<210> SEQ ID NO 2
<211> LENGTH: 23
<212> TYPE: PRT
<213> ORGANISM: Pasteurella multocida

<400> SEQUENCE: 2

Asn Tyr Tyr Asp Ile Thr Leu Ala Leu Ala Gly Val Cys Gln Ala Ala
1               5                   10                  15

Lys Leu Val Gln Gln Phe Ala
            20

<210> SEQ ID NO 3
<211> LENGTH: 23
<212> TYPE: PRT
<213> ORGANISM: Escherichia coli

<400> SEQUENCE: 3

Asn Tyr Tyr Asp Ile Thr Leu Ala Leu Ala Gly Ile Cys Gln Ser Ala
1               5                   10                  15

Arg Leu Val Gln Gln Leu Ala
            20

<210> SEQ ID NO 4
<211> LENGTH: 23
<212> TYPE: PRT
<213> ORGANISM: Vibrio cholerae

<400> SEQUENCE: 4

Ala Ile Tyr Asp Arg Thr Ile Ala Phe Ala Gly Ile Cys Gln Ala Val
1               5                   10                  15

Ala Leu Val Gln Gln Val Ala
            20

<210> SEQ ID NO 5
<211> LENGTH: 23
<212> TYPE: PRT
<213> ORGANISM: Buchnera aphidicola

<400> SEQUENCE: 5

Lys Ile His Leu Ile Thr Leu Ser Leu Ala Gly Ile Cys Gln Ser Ala
1               5                   10                  15

His Leu Val Gln Gln Leu Ala
            20

<210> SEQ ID NO 6
<211> LENGTH: 23
<212> TYPE: PRT
<213> ORGANISM: Pseudomonas aeruginosa -continued

```
<400> SEQUENCE: 6

Asp Pro Arg Gln Gln Leu Ile Ala Leu Gly Ala Val Phe Glu Ser Ala
1               5                   10                  15

Ala Leu Val Asp Lys Leu Ala
            20

<210> SEQ ID NO 7
<211> LENGTH: 23
<212> TYPE: PRT
<213> ORGANISM: Xylella fastidiosa

<400> SEQUENCE: 7

Leu Ile Asp Asn Arg Val Leu Ala Leu Ala Gly Val Val Gln Ala Leu
1               5                   10                  15

Gln Gln Val Arg Gln Ile Ala
            20

<210> SEQ ID NO 8
<211> LENGTH: 23
<212> TYPE: PRT
<213> ORGANISM: Rhizobium loti

<400> SEQUENCE: 8

Asn Leu Pro Pro Ile Val Leu Ala Val Ile Gly Ile Cys Ala Ala Val
1               5                   10                  15

Phe Leu Leu Gln Gln Tyr Val
            20

<210> SEQ ID NO 9
<211> LENGTH: 23
<212> TYPE: PRT
<213> ORGANISM: Homo sapiens

<400> SEQUENCE: 9

Asn Tyr Phe Ile Val Asn Leu Ala Leu Ala Asp Leu Cys Met Ala Ala
1               5                   10                  15

Phe Asn Ala Ala Phe Asn Phe
            20

<210> SEQ ID NO 10
<211> LENGTH: 23
<212> TYPE: PRT
<213> ORGANISM: Chlamydia pneumoniae

<400> SEQUENCE: 10

Thr Ala Phe Asp Phe Asn Lys Met Leu Asp Gly Val Cys Thr Tyr Val
1               5                   10                  15

Lys Gly Val Gln Gln Tyr Leu
            20

<210> SEQ ID NO 11
<211> LENGTH: 23
<212> TYPE: PRT
<213> ORGANISM: Rhizobium loti

<400> SEQUENCE: 11

Arg Ala Ile Leu Ile Pro Leu Ala Leu Ala Gly Leu Cys Gln Val Ala
1               5                   10                  15

Arg Ala Gly Asp Ile Ser Ser
            20
```

```
<210> SEQ ID NO 12
<211> LENGTH: 25
<212> TYPE: PRT
<213> ORGANISM: Bacillus subtilis

<400> SEQUENCE: 12

Met Arg Asn Leu Thr Lys Thr Ser Leu Leu Ala Gly Leu Cys Thr
1               5                   10                  15

Ala Ala Gln Met Val Phe Val Thr His
            20                  25

<210> SEQ ID NO 13
<211> LENGTH: 25
<212> TYPE: PRT
<213> ORGANISM: Kingella denitrificans

<400> SEQUENCE: 13

Ile Glu Leu Met Ile Val Ile Ala Ile Ile Gly Ile Leu Ala Ala Ile
1               5                   10                  15

Ala Leu Pro Ala Tyr Gln Glu Tyr Val
            20                  25

<210> SEQ ID NO 14
<211> LENGTH: 25
<212> TYPE: PRT
<213> ORGANISM: Eikenella corrodens

<400> SEQUENCE: 14

Ile Glu Leu Met Ile Val Ile Ala Ile Ile Gly Ile Leu Ala Ala Ile
1               5                   10                  15

Ala Leu Pro Ala Tyr Gln Asp Tyr Val
            20                  25

<210> SEQ ID NO 15
<211> LENGTH: 16
<212> TYPE: PRT
<213> ORGANISM: zonula occludens toxin

<400> SEQUENCE: 15

Ala Ser Phe Gly Phe Cys Ile Gly Arg Leu Cys Val Gln Asp Gly Phe
1               5                   10                  15

<210> SEQ ID NO 16
<211> LENGTH: 6
<212> TYPE: PRT
<213> ORGANISM: Artificial
<220> FEATURE:
<223> OTHER INFORMATION: Linker

<400> SEQUENCE: 16

Gly Gly Lys Gly Gly Lys
1               5

<210> SEQ ID NO 17
<211> LENGTH: 5
<212> TYPE: PRT
<213> ORGANISM: Artificial
<220> FEATURE:
<223> OTHER INFORMATION: Fully conserved "strong" amino acid residue
      chain

<400> SEQUENCE: 17

Asn Arg Glu Gln Lys
1               5
```

<210> SEQ ID NO 18
<211> LENGTH: 4
<212> TYPE: PRT
<213> ORGANISM: Artificial
<220> FEATURE:
<223> OTHER INFORMATION: Fully conserved "strong" amino acid residue
      chain

<400> SEQUENCE: 18

Asn His Gln Lys
1

<210> SEQ ID NO 19
<211> LENGTH: 4
<212> TYPE: PRT
<213> ORGANISM: Artificial
<220> FEATURE:
<223> OTHER INFORMATION: Fully conserved "strong" amino acid residue
      chain

<400> SEQUENCE: 19

Asn Asp Glu Gln
1

<210> SEQ ID NO 20
<211> LENGTH: 4
<212> TYPE: PRT
<213> ORGANISM: Artificial
<220> FEATURE:
<223> OTHER INFORMATION: Fully conserved "strong" amino acid residue
      chain

<400> SEQUENCE: 20

Gln His Arg Lys
1

<210> SEQ ID NO 21
<211> LENGTH: 4
<212> TYPE: PRT
<213> ORGANISM: Artificial
<220> FEATURE:
<223> OTHER INFORMATION: Fully conserved "strong" amino acid residue
      chain

<400> SEQUENCE: 21

Met Ile Leu Val
1

<210> SEQ ID NO 22
<211> LENGTH: 30
<212> TYPE: PRT
<213> ORGANISM: Artificial
<220> FEATURE:
<223> OTHER INFORMATION: Penetrating peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: PEPTIDE
<222> LOCATION: (30)..(30)
<223> OTHER INFORMATION: wherein Xaa is Lysine-NH2

<400> SEQUENCE: 22

Asn Tyr Tyr Asp Ile Thr Leu Ala Leu Ala Gly Ile Cys Gln Ser Ala
1               5                   10                  15

Arg Leu Val Gln Gln Leu Ala Gly Gly Gly Lys Gly Gly Xaa 20                  25                  30

<210> SEQ ID NO 23
<211> LENGTH: 4
<212> TYPE: PRT
<213> ORGANISM: Artificial
<220> FEATURE:
<223> OTHER INFORMATION: Fully conserved "strong" amino acid residue
      chain

<400> SEQUENCE: 23

Met Ile Leu Phe
1

<210> SEQ ID NO 24
<211> LENGTH: 23
<212> TYPE: PRT
<213> ORGANISM: Homo sapiens

<400> SEQUENCE: 24

Asn Tyr Phe Leu Val Asn Leu Ala Phe Ala Glu Ala Ser Met Ala Ala
1               5                  10                  15

Phe Asn Thr Val Val Asn Phe
            20

<210> SEQ ID NO 25
<211> LENGTH: 24
<212> TYPE: PRT
<213> ORGANISM: Escherichia coli

<400> SEQUENCE: 25

Met Asn Tyr Tyr Asp Ile Thr Leu Ala Leu Ala Gly Ile Cys Gln Ser
1               5                  10                  15

Ala Arg Leu Val Gln Gln Leu Ala
            20

<210> SEQ ID NO 26
<211> LENGTH: 23
<212> TYPE: PRT
<213> ORGANISM: Escherichia coli

<400> SEQUENCE: 26

Met Tyr Tyr Asp Ile Thr Leu Ala Leu Ala Gly Ile Cys Gln Ser Ala
1               5                  10                  15

Arg Leu Val Gln Gln Leu Ala
            20

<210> SEQ ID NO 27
<211> LENGTH: 22
<212> TYPE: PRT
<213> ORGANISM: Escherichia coli

<400> SEQUENCE: 27

Met Tyr Asp Ile Thr Leu Ala Leu Ala Gly Ile Cys Gln Ser Ala Arg
1               5                  10                  15

Leu Val Gln Gln Leu Ala
            20

<210> SEQ ID NO 28
<211> LENGTH: 23
<212> TYPE: PRT
<213> ORGANISM: Bacillus subtilis

<400> SEQUENCE: 28

```
Met Arg Asn Leu Thr Arg Thr Ser Leu Leu Leu Ala Gly Leu Cys Thr
1               5                   10                  15

Ala Ala Gln Met Val Phe Val
            20
```

<210> SEQ ID NO 29
<211> LENGTH: 23
<212> TYPE: PRT
<213> ORGANISM: Haemophilus influenzae

<400> SEQUENCE: 29

```
Asn Tyr His Asp Ile Val Leu Ala Leu Ala Gly Val Cys Gln Ser Ala
1               5                   10                  15

Arg Leu Val His Gln Leu Ala
            20
```

<210> SEQ ID NO 30
<211> LENGTH: 30
<212> TYPE: PRT
<213> ORGANISM: Artificial
<220> FEATURE:
<223> OTHER INFORMATION: Penetrating peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: PEPTIDE
<222> LOCATION: (30)..(30)
<223> OTHER INFORMATION: wherein Xaa is Lysine-NH2

<400> SEQUENCE: 30

```
Asn Leu Pro Pro Ile Val Leu Ala Val Ile Gly Ile Cys Ala Ala Val
1               5                   10                  15

Phe Leu Leu Gln Gln Tyr Val Gly Gly Gly Lys Gly Gly Xaa
            20                  25                  30
```

<210> SEQ ID NO 31
<211> LENGTH: 30
<212> TYPE: PRT
<213> ORGANISM: Artificial
<220> FEATURE:
<223> OTHER INFORMATION: Penetrating peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: PEPTIDE
<222> LOCATION: (30)..(30)
<223> OTHER INFORMATION: wherein Xaa is Lysine -NH2

<400> SEQUENCE: 31

```
Asn Tyr Phe Ile Val Asn Leu Ala Leu Ala Asp Leu Cys Met Ala Ala
1               5                   10                  15

Phe Asn Ala Ala Phe Asn Phe Gly Gly Gly Lys Gly Gly Xaa
            20                  25                  30
```

<210> SEQ ID NO 32
<211> LENGTH: 30
<212> TYPE: PRT
<213> ORGANISM: Artificial
<220> FEATURE:
<223> OTHER INFORMATION: Penetrating peptide
<220> FEATURE:
<221> NAME/KEY: MOD_RES
<222> LOCATION: (1)..(1)

```
<223> OTHER INFORMATION: ACETYLATION
<220> FEATURE:
<221> NAME/KEY: PEPTIDE
<222> LOCATION: (30)..(30)
<223> OTHER INFORMATION: wherein Xaa is Lysine-NH2

<400> SEQUENCE: 32

Met Arg Asn Leu Thr Arg Thr Ser Leu Leu Leu Ala Gly Leu Cys Thr
1               5                   10                  15

Ala Ala Gln Met Val Phe Val Gly Gly Gly Lys Gly Gly Xaa
            20                  25                  30

<210> SEQ ID NO 33
<211> LENGTH: 29
<212> TYPE: PRT
<213> ORGANISM: Artificial
<220> FEATURE:
<223> OTHER INFORMATION: Penetrating peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: PEPTIDE
<222> LOCATION: (29)..(29)
<223> OTHER INFORMATION: wherein Xaa is Lysine-NH2

<400> SEQUENCE: 33

Asn Tyr His Asp Ile Val Leu Ala Leu Ala Gly Val Cys Gln Ser Ala
1               5                   10                  15

Arg Leu Val His Gln Leu Ala Gly Gly Lys Gly Gly Xaa
            20                  25

<210> SEQ ID NO 34
<211> LENGTH: 29
<212> TYPE: PRT
<213> ORGANISM: Artificial
<220> FEATURE:
<223> OTHER INFORMATION: Penetrating peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: PEPTIDE
<222> LOCATION: (29)..(29)
<223> OTHER INFORMATION: wherein Xaa is Lysine-NH2

<400> SEQUENCE: 34

Asn Tyr Phe Leu Val Asn Leu Ala Phe Ala Glu Ala Ser Met Ala Ala
1               5                   10                  15

Phe Asn Thr Val Val Asn Phe Gly Gly Lys Gly Gly Xaa
            20                  25

<210> SEQ ID NO 35
<211> LENGTH: 31
<212> TYPE: PRT
<213> ORGANISM: Artificial
<220> FEATURE:
<223> OTHER INFORMATION: Penetrating peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: PEPTIDE
<222> LOCATION: (31)..(31)
<223> OTHER INFORMATION: wherein Xaa is Lysine-NH2

<400> SEQUENCE: 35
```

-continued

```
Met Asn Tyr Tyr Asp Ile Thr Leu Ala Leu Ala Gly Ile Cys Gln Ser
1               5                   10                  15

Ala Arg Leu Val Gln Gln Leu Ala Gly Gly Lys Gly Gly Xaa
            20                  25                  30
```

<210> SEQ ID NO 36
<211> LENGTH: 30
<212> TYPE: PRT
<213> ORGANISM: Artificial
<220> FEATURE:
<223> OTHER INFORMATION: Penetrating peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: PEPTIDE
<222> LOCATION: (30)..(30)
<223> OTHER INFORMATION: wherein Xaa is Lysine-NH2

<400> SEQUENCE: 36

```
Met Tyr Tyr Asp Ile Thr Leu Ala Leu Ala Gly Ile Cys Gln Ser Ala
1               5                   10                  15

Arg Leu Val Gln Gln Leu Ala Gly Gly Gly Lys Gly Gly Xaa
            20                  25                  30
```

<210> SEQ ID NO 37
<211> LENGTH: 29
<212> TYPE: PRT
<213> ORGANISM: Artificial
<220> FEATURE:
<223> OTHER INFORMATION: Penetrating peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: PEPTIDE
<222> LOCATION: (29)..(29)
<223> OTHER INFORMATION: wherein Xaa is Lysine-NH2

<400> SEQUENCE: 37

```
Met Tyr Asp Ile Thr Leu Ala Leu Ala Gly Ile Cys Gln Ser Ala Arg
1               5                   10                  15

Leu Val Gln Gln Leu Ala Gly Gly Gly Lys Gly Gly Xaa
            20                  25
```

<210> SEQ ID NO 38
<211> LENGTH: 4
<212> TYPE: PRT
<213> ORGANISM: Artificial
<220> FEATURE:
<223> OTHER INFORMATION: Fully conserved "weak" amino acid residue
      chain

<400> SEQUENCE: 38

```
Ser Thr Asn Lys
1
```

<210> SEQ ID NO 39
<211> LENGTH: 4
<212> TYPE: PRT
<213> ORGANISM: Artificial
<220> FEATURE:
<223> OTHER INFORMATION: Fully conserved "weak" amino acid residue
      chain

<400> SEQUENCE: 39

```
Ser Thr Pro Ala
1

<210> SEQ ID NO 40
<211> LENGTH: 4
<212> TYPE: PRT
<213> ORGANISM: Artificial
<220> FEATURE:
<223> OTHER INFORMATION: Fully conserved "weak" amino acid residue
      chain

<400> SEQUENCE: 40

Ser Gly Asn Asp
1

<210> SEQ ID NO 41
<211> LENGTH: 6
<212> TYPE: PRT
<213> ORGANISM: Artificial
<220> FEATURE:
<223> OTHER INFORMATION: Fully conserved "weak" amino acid residue
      chain

<400> SEQUENCE: 41

Ser Asn Asp Glu Gln Lys
1               5

<210> SEQ ID NO 42
<211> LENGTH: 6
<212> TYPE: PRT
<213> ORGANISM: Artificial
<220> FEATURE:
<223> OTHER INFORMATION: Fully conserved "weak" amino acid residue
      chain

<400> SEQUENCE: 42

Asn Asp Glu Gln His Lys
1               5

<210> SEQ ID NO 43
<211> LENGTH: 6
<212> TYPE: PRT
<213> ORGANISM: Artificial
<220> FEATURE:
<223> OTHER INFORMATION: Fully conserved "weak" amino acid residue
      chain

<400> SEQUENCE: 43

Asn Glu Gln His Arg Lys
1               5

<210> SEQ ID NO 44
<211> LENGTH: 16
<212> TYPE: PRT
<213> ORGANISM: Artificial
<220> FEATURE:
<223> OTHER INFORMATION: Penetrating peptide
<220> FEATURE:
<221> NAME/KEY: VARIANT
<222> LOCATION: (1)..(1)
<223> OTHER INFORMATION: wherein Xaa is a hydrophobic amino acid
<220> FEATURE:
<221> NAME/KEY: variant
<222> LOCATION: (2)..(2)
<223> OTHER INFORMATION: wherein Xaa is any amino acid
<220> FEATURE:
<221> NAME/KEY: variant
<222> LOCATION: (3)..(3)
<223> OTHER INFORMATION: wherein Xaa is a hydrophobic amino acid
```

```
<220> FEATURE:
<221> NAME/KEY: variant
<222> LOCATION: (4)..(4)
<223> OTHER INFORMATION: wherein Xaa is any amino acid
<220> FEATURE:
<221> NAME/KEY: variant
<222> LOCATION: (5)..(5)
<223> OTHER INFORMATION: wherein Xaa is a hydrophobic amino acid
<220> FEATURE:
<221> NAME/KEY: variant
<222> LOCATION: (6)..(6)
<223> OTHER INFORMATION: wherein Xaa is any amino acid
<220> FEATURE:
<221> NAME/KEY: variant
<222> LOCATION: (7)..(7)
<223> OTHER INFORMATION: wherein Xaa is a hydrophobic amino acid
<220> FEATURE:
<221> NAME/KEY: variant
<222> LOCATION: (8)..(8)
<223> OTHER INFORMATION: wherein Xaa is any amino acid
<220> FEATURE:
<221> NAME/KEY: variant
<222> LOCATION: (9)..(9)
<223> OTHER INFORMATION: wherein Xaa is a charged amino acid
<220> FEATURE:
<221> NAME/KEY: variant
<222> LOCATION: (10)..(10)
<223> OTHER INFORMATION: wherein Xaa is a hydrophobic amino acid
<220> FEATURE:
<221> NAME/KEY: variant
<222> LOCATION: (11)..(11)
<223> OTHER INFORMATION: wherein Xaa is any amino acid
<220> FEATURE:
<221> NAME/KEY: variant
<222> LOCATION: (12)..(12)
<223> OTHER INFORMATION: wherein Xaa is a hydrophobic amino acid
<220> FEATURE:
<221> NAME/KEY: variant
<222> LOCATION: (13)..(13)
<223> OTHER INFORMATION: wherein Xaa is any amino acid
<220> FEATURE:
<221> NAME/KEY: variant
<222> LOCATION: (14)..(14)
<223> OTHER INFORMATION: wherein Xaa is a charged amino acid
<220> FEATURE:
<221> NAME/KEY: variant
<222> LOCATION: (15)..(15)
<223> OTHER INFORMATION: wherein Xaa is any amino acid
<220> FEATURE:
<221> NAME/KEY: variant
<222> LOCATION: (16)..(16)
<223> OTHER INFORMATION: wherein Xaa is a hydrophobic amino acid

<400> SEQUENCE: 44

Xaa Xaa Xaa Xaa Xaa Xaa Xaa Xaa Xaa Xaa Xaa Xaa Xaa Xaa Xaa Xaa
1               5                   10                  15

<210> SEQ ID NO 45
<211> LENGTH: 23
<212> TYPE: PRT
<213> ORGANISM: Artificial
<220> FEATURE:
<223> OTHER INFORMATION: Penetrating peptide
<220> FEATURE:
<221> NAME/KEY: variant
<222> LOCATION: (1)..(1)
<223> OTHER INFORMATION: wherein Xaa is a charged amino acid
<220> FEATURE:
<221> NAME/KEY: variant
<222> LOCATION: (2)..(2)
<223> OTHER INFORMATION: wherein Xaa is a hydrophobic amino acid
<220> FEATURE:
<221> NAME/KEY: variant
<222> LOCATION: (3)..(3)
<223> OTHER INFORMATION: wherein Xaa is any amino acid
<220> FEATURE:
<221> NAME/KEY: variant
```

```
<222> LOCATION: (4)..(5)
<223> OTHER INFORMATION: wherein Xaa is a hydrophobic amino acid
<220> FEATURE:
<221> NAME/KEY: variant
<222> LOCATION: (6)..(6)
<223> OTHER INFORMATION: wherein Xaa is any amino acid
<220> FEATURE:
<221> NAME/KEY: variant
<222> LOCATION: (7)..(7)
<223> OTHER INFORMATION: wherein Xaa is a hydrophobic amino acid
<220> FEATURE:
<221> NAME/KEY: variant
<222> LOCATION: (8)..(8)
<223> OTHER INFORMATION: wherein Xaa is any amino acid
<220> FEATURE:
<221> NAME/KEY: variant
<222> LOCATION: (9)..(10)
<223> OTHER INFORMATION: wherein Xaa is a hydrophobic amino acid
<220> FEATURE:
<221> NAME/KEY: variant
<222> LOCATION: (11)..(11)
<223> OTHER INFORMATION: wherein Xaa is any amino acid
<220> FEATURE:
<221> NAME/KEY: variant
<222> LOCATION: (12)..(12)
<223> OTHER INFORMATION: wherein Xaa is a hydrophobic amino acid
<220> FEATURE:
<221> NAME/KEY: variant
<222> LOCATION: (13)..(15)
<223> OTHER INFORMATION: wherein Xaa is any amino acid
<220> FEATURE:
<221> NAME/KEY: variant
<222> LOCATION: (16)..(16)
<223> OTHER INFORMATION: wherein Xaa is a hydrophobic amino acid
<220> FEATURE:
<221> NAME/KEY: variant
<222> LOCATION: (17)..(17)
<223> OTHER INFORMATION: wherein Xaa is any amino acid
<220> FEATURE:
<221> NAME/KEY: variant
<222> LOCATION: (18)..(19)
<223> OTHER INFORMATION: wherein Xaa is a hydrophobic amino acid
<220> FEATURE:
<221> NAME/KEY: variant
<222> LOCATION: (20)..(21)
<223> OTHER INFORMATION: wherein Xaa is any amino acid
<220> FEATURE:
<221> NAME/KEY: variant
<222> LOCATION: (22)..(23)
<223> OTHER INFORMATION: wherein Xaa is a hydrophobic amino acid

<400> SEQUENCE: 45

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 46
<211> LENGTH: 23
<212> TYPE: PRT
<213> ORGANISM: Artificial
<220> FEATURE:
<223> OTHER INFORMATION: Penetrating peptide
<220> FEATURE:
<221> NAME/KEY: variant
<222> LOCATION: (1)..(1)
<223> OTHER INFORMATION: wherein Xaa is a charged amino acid
<220> FEATURE:
<221> NAME/KEY: variant
<222> LOCATION: (2)..(2)
<223> OTHER INFORMATION: wherein Xaa is a hydrophobic amino acid
<220> FEATURE:
<221> NAME/KEY: variant
<222> LOCATION: (3)..(3)
<223> OTHER INFORMATION: wherein Xaa is a charged amino acid
<220> FEATURE:
```

```
<221> NAME/KEY: variant
<222> LOCATION: (4)..(5)
<223> OTHER INFORMATION: wherein Xaa is any amino acid
<220> FEATURE:
<221> NAME/KEY: variant
<222> LOCATION: (6)..(9)
<223> OTHER INFORMATION: wherein Xaa is a hydrophobic amino acid
<220> FEATURE:
<221> NAME/KEY: variant
<222> LOCATION: (10)..(10)
<223> OTHER INFORMATION: wherein Xaa is any amino acid
<220> FEATURE:
<221> NAME/KEY: variant
<222> LOCATION: (11)..(13)
<223> OTHER INFORMATION: wherein Xaa is a hydrophobic amino acid
<220> FEATURE:
<221> NAME/KEY: variant
<222> LOCATION: (14)..(14)
<223> OTHER INFORMATION: wherein Xaa is a charged amino acid
<220> FEATURE:
<221> NAME/KEY: variant
<222> LOCATION: (15)..(15)
<223> OTHER INFORMATION: wherein Xaa is any amino acid
<220> FEATURE:
<221> NAME/KEY: variant
<222> LOCATION: (16)..(19)
<223> OTHER INFORMATION: wherein Xaa is a hydrophobic amino acid
<220> FEATURE:
<221> NAME/KEY: variant
<222> LOCATION: (20)..(21)
<223> OTHER INFORMATION: wherein Xaa is a charged amino acid
<220> FEATURE:
<221> NAME/KEY: variant
<222> LOCATION: (22)..(23)
<223> OTHER INFORMATION: wherein Xaa is a hydrophobic amino acid

<400> SEQUENCE: 46

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 47
<211> LENGTH: 23
<212> TYPE: PRT
<213> ORGANISM: Artificial
<220> FEATURE:
<223> OTHER INFORMATION: Penetrating peptide
<220> FEATURE:
<221> NAME/KEY: variant
<222> LOCATION: (1)..(1)
<223> OTHER INFORMATION: wherein Xaa is a charged amino acid
<220> FEATURE:
<221> NAME/KEY: variant
<222> LOCATION: (2)..(10)
<223> OTHER INFORMATION: wherein Xaa is a hydrophobic amino acid
<220> FEATURE:
<221> NAME/KEY: variant
<222> LOCATION: (11)..(11)
<223> OTHER INFORMATION: wherein Xaa is any amino acid
<220> FEATURE:
<221> NAME/KEY: variant
<222> LOCATION: (12)..(12)
<223> OTHER INFORMATION: wherein Xaa is a hydrophobic amino acid
<220> FEATURE:
<221> NAME/KEY: variant
<222> LOCATION: (13)..(14)
<223> OTHER INFORMATION: wherein Xaa is any amino acid
<220> FEATURE:
<221> NAME/KEY: variant
<222> LOCATION: (15)..(16)
<223> OTHER INFORMATION: wherein Xaa is a hydrophobic amino acid
<220> FEATURE:
<221> NAME/KEY: variant
<222> LOCATION: (17)..(17)
<223> OTHER INFORMATION: wherein Xaa is a charged amino acid
```

```
<220> FEATURE:
<221> NAME/KEY: variant
<222> LOCATION: (18)..(18)
<223> OTHER INFORMATION: wherein Xaa is a hydrophobic amino acid
<220> FEATURE:
<221> NAME/KEY: variant
<222> LOCATION: (19)..(19)
<223> OTHER INFORMATION: wherein Xaa is any amino acid
<220> FEATURE:
<221> NAME/KEY: variant
<222> LOCATION: (20)..(20)
<223> OTHER INFORMATION: wherein Xaa is a charged amino acid
<220> FEATURE:
<221> NAME/KEY: variant
<222> LOCATION: (21)..(21)
<223> OTHER INFORMATION: wherein Xaa is a hydrophobic amino acid
<220> FEATURE:
<221> NAME/KEY: variant
<222> LOCATION: (22)..(23)
<223> OTHER INFORMATION: wherein Xaa is any amino acid

<400> SEQUENCE: 47

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 48
<211> LENGTH: 25
<212> TYPE: PRT
<213> ORGANISM: Artificial
<220> FEATURE:
<223> OTHER INFORMATION: Penetrating peptide
<220> FEATURE:
<221> NAME/KEY: variant
<222> LOCATION: (1)..(1)
<223> OTHER INFORMATION: wherein Xaa is a hydrophobic amino acid
<220> FEATURE:
<221> NAME/KEY: variant
<222> LOCATION: (2)..(2)
<223> OTHER INFORMATION: wherein Xaa is a charged amino acid
<220> FEATURE:
<221> NAME/KEY: variant
<222> LOCATION: (3)..(10)
<223> OTHER INFORMATION: wherein Xaa is a hydrophobic amino acid
<220> FEATURE:
<221> NAME/KEY: variant
<222> LOCATION: (11)..(11)
<223> OTHER INFORMATION: wherein Xaa is any amino acid
<220> FEATURE:
<221> NAME/KEY: variant
<222> LOCATION: (12)..(20)
<223> OTHER INFORMATION: wherein Xaa is a hydrophobic amino acid
<220> FEATURE:
<221> NAME/KEY: variant
<222> LOCATION: (21)..(22)
<223> OTHER INFORMATION: wherein Xaa is any amino acid
<220> FEATURE:
<221> NAME/KEY: variant
<222> LOCATION: (23)..(23)
<223> OTHER INFORMATION: wherein Xaa is a charged amino acid
<220> FEATURE:
<221> NAME/KEY: variant
<222> LOCATION: (24)..(24)
<223> OTHER INFORMATION: wherein Xaa is any amino acid
<220> FEATURE:
<221> NAME/KEY: variant
<222> LOCATION: (25)..(25)
<223> OTHER INFORMATION: wherein Xaa is a hydrophobic amino acid

<400> SEQUENCE: 48

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
```

<210> SEQ ID NO 49
<211> LENGTH: 23
<212> TYPE: PRT
<213> ORGANISM: Artificial
<220> FEATURE:
<223> OTHER INFORMATION: Penetrating peptide
<220> FEATURE:
<221> NAME/KEY: variant
<222> LOCATION: (1)..(2)
<223> OTHER INFORMATION: wherein Xaa is a hydrophobic amino acid
<220> FEATURE:
<221> NAME/KEY: variant
<222> LOCATION: (3)..(3)
<223> OTHER INFORMATION: wherein Xaa is a charged amino acid
<220> FEATURE:
<221> NAME/KEY: variant
<222> LOCATION: (4)..(4)
<223> OTHER INFORMATION: wherein Xaa is any amino acid
<220> FEATURE:
<221> NAME/KEY: variant
<222> LOCATION: (5)..(5)
<223> OTHER INFORMATION: wherein Xaa is a charged amino acid
<220> FEATURE:
<221> NAME/KEY: variant
<222> LOCATION: (6)..(10)
<223> OTHER INFORMATION: wherein Xaa is a hydrophobic amino acid
<220> FEATURE:
<221> NAME/KEY: variant
<222> LOCATION: (11)..(11)
<223> OTHER INFORMATION: wherein Xaa is any amino acid
<220> FEATURE:
<221> NAME/KEY: variant
<222> LOCATION: (12)..(13)
<223> OTHER INFORMATION: wherein Xaa is a hydrophobic amino acid
<220> FEATURE:
<221> NAME/KEY: variant
<222> LOCATION: (14)..(14)
<223> OTHER INFORMATION: wherein Xaa is any amino acid
<220> FEATURE:
<221> NAME/KEY: variant
<222> LOCATION: (15)..(16)
<223> OTHER INFORMATION: wherein Xaa is a hydrophobic amino acid
<220> FEATURE:
<221> NAME/KEY: variant
<222> LOCATION: (17)..(18)
<223> OTHER INFORMATION: wherein Xaa is any amino acid
<220> FEATURE:
<221> NAME/KEY: variant
<222> LOCATION: (19)..(19)
<223> OTHER INFORMATION: wherein Xaa is a hydrophobic amino acid
<220> FEATURE:
<221> NAME/KEY: variant
<222> LOCATION: (20)..(20)
<223> OTHER INFORMATION: wherein Xaa is a charged amino acid
<220> FEATURE:
<221> NAME/KEY: variant
<222> LOCATION: (21)..(21)
<223> OTHER INFORMATION: wherein Xaa is any amino acid
<220> FEATURE:
<221> NAME/KEY: variant
<222> LOCATION: (22)..(23)
<223> OTHER INFORMATION: wherein Xaa is any amino acid

<400> SEQUENCE: 49

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 50
<211> LENGTH: 23
<212> TYPE: PRT
<213> ORGANISM: Artificial

```
<220> FEATURE:
<223> OTHER INFORMATION: Penetrating peptide
<220> FEATURE:
<221> NAME/KEY: variant
<222> LOCATION: (1)..(1)
<223> OTHER INFORMATION: wherein Xaa is any amino acid
<220> FEATURE:
<221> NAME/KEY: variant
<222> LOCATION: (2)..(10)
<223> OTHER INFORMATION: wherein Xaa is a hydrophobic amino acid
<220> FEATURE:
<221> NAME/KEY: variant
<222> LOCATION: (11)..(11)
<223> OTHER INFORMATION: wherein Xaa is any amino acid
<220> FEATURE:
<221> NAME/KEY: variant
<222> LOCATION: (12)..(12)
<223> OTHER INFORMATION: wherein Xaa is a hydrophobic amino acid
<220> FEATURE:
<221> NAME/KEY: variant
<222> LOCATION: (13)..(13)
<223> OTHER INFORMATION: wherein Xaa is any amino acid
<220> FEATURE:
<221> NAME/KEY: variant
<222> LOCATION: (14)..(19)
<223> OTHER INFORMATION: wherein Xaa is a hydrophobic amino acid
<220> FEATURE:
<221> NAME/KEY: variant
<222> LOCATION: (20)..(22)
<223> OTHER INFORMATION: wherein Xaa is any amino acid
<220> FEATURE:
<221> NAME/KEY: variant
<222> LOCATION: (23)..(23)
<223> OTHER INFORMATION: wherein Xaa is a hydrophobic amino acid

<400> SEQUENCE: 50

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 51
<211> LENGTH: 23
<212> TYPE: PRT
<213> ORGANISM: Artificial
<220> FEATURE:
<223> OTHER INFORMATION: Penetrating peptide
<220> FEATURE:
<221> NAME/KEY: variant
<222> LOCATION: (1)..(2)
<223> OTHER INFORMATION: wherein Xaa is any amino acid
<220> FEATURE:
<221> NAME/KEY: variant
<222> LOCATION: (3)..(5)
<223> OTHER INFORMATION: wherein Xaa is a hydrophobic amino acid
<220> FEATURE:
<221> NAME/KEY: variant
<222> LOCATION: (6)..(6)
<223> OTHER INFORMATION: wherein Xaa is any amino acid
<220> FEATURE:
<221> NAME/KEY: variant
<222> LOCATION: (7)..(10)
<223> OTHER INFORMATION: wherein Xaa is a hydrophobic amino acid
<220> FEATURE:
<221> NAME/KEY: variant
<222> LOCATION: (11)..(11)
<223> OTHER INFORMATION: wherein Xaa is a charged amino acid
<220> FEATURE:
<221> NAME/KEY: variant
<222> LOCATION: (12)..(12)
<223> OTHER INFORMATION: wherein Xaa is a hydrophobic amino acid
<220> FEATURE:
<221> NAME/KEY: variant
<222> LOCATION: (13)..(13)
<223> OTHER INFORMATION: wherein Xaa is any amino acid
<220> FEATURE:
```

```
<221> NAME/KEY: variant
<222> LOCATION: (14)..(17)
<223> OTHER INFORMATION: wherein Xaa is a hydrophobic amino acid
<220> FEATURE:
<221> NAME/KEY: variant
<222> LOCATION: (18)..(18)
<223> OTHER INFORMATION: wherein Xaa is any amino acid
<220> FEATURE:
<221> NAME/KEY: variant
<222> LOCATION: (19)..(20)
<223> OTHER INFORMATION: wherein Xaa is a hydrophobic amino acid
<220> FEATURE:
<221> NAME/KEY: variant
<222> LOCATION: (21)..(21)
<223> OTHER INFORMATION: wherein Xaa is a hydrophobic amino acid, or no
      amino acid
<220> FEATURE:
<221> NAME/KEY: variant
<222> LOCATION: (22)..(22)
<223> OTHER INFORMATION: wherein Xaa is any amino acid
<220> FEATURE:
<221> NAME/KEY: variant
<222> LOCATION: (23)..(23)
<223> OTHER INFORMATION: wherein Xaa is a hydrophobic amino acid

<400> SEQUENCE: 51

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 52
<211> LENGTH: 24
<212> TYPE: PRT
<213> ORGANISM: Artificial
<220> FEATURE:
<223> OTHER INFORMATION: Penetrating peptide
<220> FEATURE:
<221> NAME/KEY: variant
<222> LOCATION: (1)..(1)
<223> OTHER INFORMATION: wherein Xaa is any amino acid
<220> FEATURE:
<221> NAME/KEY: variant
<222> LOCATION: (2)..(3)
<223> OTHER INFORMATION: wherein Xaa is a hydrophobic amino acid
<220> FEATURE:
<221> NAME/KEY: variant
<222> LOCATION: (4)..(4)
<223> OTHER INFORMATION: wherein Xaa is any amino acid
<220> FEATURE:
<221> NAME/KEY: variant
<222> LOCATION: (5)..(5)
<223> OTHER INFORMATION: wherein Xaa is a charged amino acid
<220> FEATURE:
<221> NAME/KEY: variant
<222> LOCATION: (6)..(6)
<223> OTHER INFORMATION: wherein Xaa is a hydrophobic amino acid
<220> FEATURE:
<221> NAME/KEY: variant
<222> LOCATION: (7)..(7)
<223> OTHER INFORMATION: wherein Xaa is any amino acid
<220> FEATURE:
<221> NAME/KEY: variant
<222> LOCATION: (8)..(8)
<223> OTHER INFORMATION: wherein Xaa is a charged amino acid
<220> FEATURE:
<221> NAME/KEY: variant
<222> LOCATION: (9)..(10)
<223> OTHER INFORMATION: wherein Xaa is a hydrophobic amino acid
<220> FEATURE:
<221> NAME/KEY: variant
<222> LOCATION: (11)..(11)
<223> OTHER INFORMATION: wherein Xaa is a charged amino acid
<220> FEATURE:
<221> NAME/KEY: variant
<222> LOCATION: (12)..(12)
```

```
<223> OTHER INFORMATION: wherein Xaa is any amino acid
<220> FEATURE:
<221> NAME/KEY: variant
<222> LOCATION: (13)..(13)
<223> OTHER INFORMATION: wherein Xaa is a hydrophobic amino acid
<220> FEATURE:
<221> NAME/KEY: variant
<222> LOCATION: (14)..(16)
<223> OTHER INFORMATION: wherein Xaa is any amino acid
<220> FEATURE:
<221> NAME/KEY: variant
<222> LOCATION: (17)..(17)
<223> OTHER INFORMATION: wherein Xaa is a hydrophobic amino acid
<220> FEATURE:
<221> NAME/KEY: variant
<222> LOCATION: (18)..(18)
<223> OTHER INFORMATION: wherein Xaa is a charged amino acid
<220> FEATURE:
<221> NAME/KEY: variant
<222> LOCATION: (19)..(19)
<223> OTHER INFORMATION: wherein Xaa is any amino acid
<220> FEATURE:
<221> NAME/KEY: variant
<222> LOCATION: (20)..(20)
<223> OTHER INFORMATION: wherein Xaa is a hydrophobic amino acid
<220> FEATURE:
<221> NAME/KEY: variant
<222> LOCATION: (21)..(23)
<223> OTHER INFORMATION: wherein Xaa is any amino acid
<220> FEATURE:
<221> NAME/KEY: variant
<222> LOCATION: (24)..(24)
<223> OTHER INFORMATION: wherein Xaa is a hydrophobic amino acid

<400> SEQUENCE: 52

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 53
<211> LENGTH: 25
<212> TYPE: PRT
<213> ORGANISM: Artificial
<220> FEATURE:
<223> OTHER INFORMATION: Penetrating peptide
<220> FEATURE:
<221> NAME/KEY: variant
<222> LOCATION: (1)..(1)
<223> OTHER INFORMATION: wherein Xaa is a hydrophobic amino acid
<220> FEATURE:
<221> NAME/KEY: variant
<222> LOCATION: (2)..(2)
<223> OTHER INFORMATION: wherein Xaa is a charged amino acid
<220> FEATURE:
<221> NAME/KEY: variant
<222> LOCATION: (3)..(3)
<223> OTHER INFORMATION: wherein Xaa is any amino acid
<220> FEATURE:
<221> NAME/KEY: variant
<222> LOCATION: (4)..(4)
<223> OTHER INFORMATION: wherein Xaa is a hydrophobic amino acid
<220> FEATURE:
<221> NAME/KEY: variant
<222> LOCATION: (5)..(5)
<223> OTHER INFORMATION: wherein Xaa is any amino acid
<220> FEATURE:
<221> NAME/KEY: variant
<222> LOCATION: (6)..(6)
<223> OTHER INFORMATION: wherein Xaa is a charged amino acid
<220> FEATURE:
<221> NAME/KEY: variant
<222> LOCATION: (7)..(8)
<223> OTHER INFORMATION: wherein Xaa is any amino acid
<220> FEATURE:
<221> NAME/KEY: variant
```

```
<222> LOCATION: (9)..(12)
<223> OTHER INFORMATION: wherein Xaa is a hydrophobic amino acid
<220> FEATURE:
<221> NAME/KEY: variant
<222> LOCATION: (13)..(13)
<223> OTHER INFORMATION: wherein Xaa is any amino acid
<220> FEATURE:
<221> NAME/KEY: variant
<222> LOCATION: (14)..(14)
<223> OTHER INFORMATION: wherein Xaa is a hydrophobic amino acid
<220> FEATURE:
<221> NAME/KEY: variant
<222> LOCATION: (15)..(16)
<223> OTHER INFORMATION: wherein Xaa is any amino acid
<220> FEATURE:
<221> NAME/KEY: variant
<222> LOCATION: (17)..(18)
<223> OTHER INFORMATION: wherein Xaa is a hydrophobic amino acid
<220> FEATURE:
<221> NAME/KEY: variant
<222> LOCATION: (19)..(19)
<223> OTHER INFORMATION: wherein Xaa is any amino acid
<220> FEATURE:
<221> NAME/KEY: variant
<222> LOCATION: (20)..(23)
<223> OTHER INFORMATION: wherein Xaa is a hydrophobic amino acid
<220> FEATURE:
<221> NAME/KEY: variant
<222> LOCATION: (24)..(25)
<223> OTHER INFORMATION: wherein Xaa is any amino acid

<400> SEQUENCE: 53

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 54
<211> LENGTH: 23
<212> TYPE: PRT
<213> ORGANISM: Artificial
<220> FEATURE:
<223> OTHER INFORMATION: Penetrating peptide
<220> FEATURE:
<221> NAME/KEY: variant
<222> LOCATION: (1)..(1)
<223> OTHER INFORMATION: wherein Xaa is a hydrophobic amino acid
<220> FEATURE:
<221> NAME/KEY: variant
<222> LOCATION: (2)..(2)
<223> OTHER INFORMATION: wherein Xaa is a charged amino acid
<220> FEATURE:
<221> NAME/KEY: variant
<222> LOCATION: (3)..(3)
<223> OTHER INFORMATION: wherein Xaa is any amino acid
<220> FEATURE:
<221> NAME/KEY: variant
<222> LOCATION: (4)..(4)
<223> OTHER INFORMATION: wherein Xaa is a hydrophobic amino acid
<220> FEATURE:
<221> NAME/KEY: variant
<222> LOCATION: (5)..(5)
<223> OTHER INFORMATION: wherein Xaa is any amino acid
<220> FEATURE:
<221> NAME/KEY: variant
<222> LOCATION: (6)..(6)
<223> OTHER INFORMATION: wherein Xaa is a charged amino acid
<220> FEATURE:
<221> NAME/KEY: variant
<222> LOCATION: (7)..(8)
<223> OTHER INFORMATION: wherein Xaa is any amino acid
<220> FEATURE:
<221> NAME/KEY: variant
<222> LOCATION: (9)..(12)
<223> OTHER INFORMATION: wherein Xaa is a hydrophobic amino acid
<220> FEATURE:
```

```
<221> NAME/KEY: variant
<222> LOCATION: (13)..(13)
<223> OTHER INFORMATION: wherein Xaa is any amino acid
<220> FEATURE:
<221> NAME/KEY: variant
<222> LOCATION: (14)..(14)
<223> OTHER INFORMATION: wherein Xaa is a hydrophobic amino acid
<220> FEATURE:
<221> NAME/KEY: variant
<222> LOCATION: (15)..(16)
<223> OTHER INFORMATION: wherein Xaa is any amino acid
<220> FEATURE:
<221> NAME/KEY: variant
<222> LOCATION: (17)..(18)
<223> OTHER INFORMATION: wherein Xaa is a hydrophobic amino acid
<220> FEATURE:
<221> NAME/KEY: variant
<222> LOCATION: (19)..(19)
<223> OTHER INFORMATION: wherein Xaa is any amino acid
<220> FEATURE:
<221> NAME/KEY: variant
<222> LOCATION: (20)..(23)
<223> OTHER INFORMATION: wherein Xaa is a hydrophobic amino acid

<400> SEQUENCE: 54

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 55
<211> LENGTH: 23
<212> TYPE: PRT
<213> ORGANISM: Artificial
<220> FEATURE:
<223> OTHER INFORMATION: Penetrating peptide
<220> FEATURE:
<221> NAME/KEY: variant
<222> LOCATION: (1)..(2)
<223> OTHER INFORMATION: wherein Xaa is a hydrophobic amino acid
<220> FEATURE:
<221> NAME/KEY: variant
<222> LOCATION: (3)..(3)
<223> OTHER INFORMATION: wherein Xaa is any amino acid
<220> FEATURE:
<221> NAME/KEY: variant
<222> LOCATION: (4)..(5)
<223> OTHER INFORMATION: wherein Xaa is a charged amino acid
<220> FEATURE:
<221> NAME/KEY: variant
<222> LOCATION: (6)..(6)
<223> OTHER INFORMATION: wherein Xaa is any amino acid
<220> FEATURE:
<221> NAME/KEY: variant
<222> LOCATION: (7)..(10)
<223> OTHER INFORMATION: wherein Xaa is a hydrophobic amino acid
<220> FEATURE:
<221> NAME/KEY: variant
<222> LOCATION: (11)..(11)
<223> OTHER INFORMATION: wherein Xaa is any amino acid
<220> FEATURE:
<221> NAME/KEY: variant
<222> LOCATION: (12)..(12)
<223> OTHER INFORMATION: wherein Xaa is a hydrophobic amino acid
<220> FEATURE:
<221> NAME/KEY: variant
<222> LOCATION: (13)..(14)
<223> OTHER INFORMATION: wherein Xaa is any amino acid
<220> FEATURE:
<221> NAME/KEY: variant
<222> LOCATION: (15)..(19)
<223> OTHER INFORMATION: wherein Xaa is a hydrophobic amino acid
<220> FEATURE:
<221> NAME/KEY: variant
<222> LOCATION: (20)..(21)
<223> OTHER INFORMATION: wherein Xaa is any amino acid
```

```
<220> FEATURE:
<221> NAME/KEY: variant
<222> LOCATION: (22)..(23)
<223> OTHER INFORMATION: wherein Xaa is a hydrophobic amino acid

<400> SEQUENCE: 55

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 56
<211> LENGTH: 26
<212> TYPE: PRT
<213> ORGANISM: Artificial
<220> FEATURE:
<223> OTHER INFORMATION: Penetrating peptide
<220> FEATURE:
<221> NAME/KEY: variant
<222> LOCATION: (1)..(1)
<223> OTHER INFORMATION: wherein Xaa is a hydrophobic amino acid, or is
      not present
<220> FEATURE:
<221> NAME/KEY: variant
<222> LOCATION: (2)..(2)
<223> OTHER INFORMATION: wherein Xaa is any amino acid
<220> FEATURE:
<221> NAME/KEY: variant
<222> LOCATION: (3)..(4)
<223> OTHER INFORMATION: wherein Xaa is any amino acid, or is not
      present
<220> FEATURE:
<221> NAME/KEY: variant
<222> LOCATION: (5)..(5)
<223> OTHER INFORMATION: wherein Xaa is a charged amino acid
<220> FEATURE:
<221> NAME/KEY: variant
<222> LOCATION: (6)..(6)
<223> OTHER INFORMATION: wherein Xaa is a hydrophobic amino acid
<220> FEATURE:
<221> NAME/KEY: variant
<222> LOCATION: (7)..(7)
<223> OTHER INFORMATION: wherein Xaa is a hydrophobic amino acid, or is
      not present
<220> FEATURE:
<221> NAME/KEY: variant
<222> LOCATION: (8)..(8)
<223> OTHER INFORMATION: wherein Xaa is any amino acid, or is not
      present
<220> FEATURE:
<221> NAME/KEY: variant
<222> LOCATION: (9)..(12)
<223> OTHER INFORMATION: wherein Xaa is a hydrophobic amino acid
<220> FEATURE:
<221> NAME/KEY: variant
<222> LOCATION: (13)..(13)
<223> OTHER INFORMATION: wherein Xaa is any amino acid
<220> FEATURE:
<221> NAME/KEY: variant
<222> LOCATION: (14)..(14)
<223> OTHER INFORMATION: wherein Xaa is a hydrophobic amino acid
<220> FEATURE:
<221> NAME/KEY: variant
<222> LOCATION: (15)..(16)
<223> OTHER INFORMATION: wherein Xaa is any amino acid
<220> FEATURE:
<221> NAME/KEY: variant
<222> LOCATION: (17)..(17)
<223> OTHER INFORMATION: wherein Xaa is any amino acid, or is not
      present
<220> FEATURE:
<221> NAME/KEY: variant
<222> LOCATION: (18)..(18)
<223> OTHER INFORMATION: wherein Xaa is a hydrophobic amino acid
<220> FEATURE:
<221> NAME/KEY: variant
```

```
<222> LOCATION: (19)..(19)
<223> OTHER INFORMATION: wherein Xaa is a hydrophobic amino acid, or is
      not present
<220> FEATURE:
<221> NAME/KEY: variant
<222> LOCATION: (20)..(20)
<223> OTHER INFORMATION: wherein Xaa is a charged amino acid
<220> FEATURE:
<221> NAME/KEY: variant
<222> LOCATION: (21)..(22)
<223> OTHER INFORMATION: wherein Xaa is a hydrophobic amino acid
<220> FEATURE:
<221> NAME/KEY: variant
<222> LOCATION: (23)..(24)
<223> OTHER INFORMATION: wherein Xaa is any amino acid
<220> FEATURE:
<221> NAME/KEY: variant
<222> LOCATION: (25)..(26)
<223> OTHER INFORMATION: wherein Xaa is a hydrophobic amino acid

<400> SEQUENCE: 56

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 57
<211> LENGTH: 28
<212> TYPE: PRT
<213> ORGANISM: Artificial
<220> FEATURE:
<223> OTHER INFORMATION: Penetrating peptide
<220> FEATURE:
<221> NAME/KEY: variant
<222> LOCATION: (1)..(2)
<223> OTHER INFORMATION: wherein Xaa is a hydrophobic amino acid
<220> FEATURE:
<221> NAME/KEY: variant
<222> LOCATION: (3)..(3)
<223> OTHER INFORMATION: wherein Xaa is a charged amino acid
<220> FEATURE:
<221> NAME/KEY: variant
<222> LOCATION: (4)..(6)
<223> OTHER INFORMATION: wherein Xaa is any amino acid
<220> FEATURE:
<221> NAME/KEY: variant
<222> LOCATION: (7)..(7)
<223> OTHER INFORMATION: wherein Xaa is a charged amino acid
<220> FEATURE:
<221> NAME/KEY: variant
<222> LOCATION: (8)..(8)
<223> OTHER INFORMATION: wherein Xaa is a hydrophobic amino acid
<220> FEATURE:
<221> NAME/KEY: variant
<222> LOCATION: (9)..(9)
<223> OTHER INFORMATION: wherein Xaa is a hydrophobic amino acid, or is
      not present
<220> FEATURE:
<221> NAME/KEY: variant
<222> LOCATION: (10)..(10)
<223> OTHER INFORMATION: wherein Xaa is any amino acid, or is not
      present
<220> FEATURE:
<221> NAME/KEY: variant
<222> LOCATION: (11)..(14)
<223> OTHER INFORMATION: wherein Xaa is a hydrophobic amino acid
<220> FEATURE:
<221> NAME/KEY: variant
<222> LOCATION: (15)..(15)
<223> OTHER INFORMATION: wherein Xaa is any amino acid
<220> FEATURE:
<221> NAME/KEY: variant
<222> LOCATION: (16)..(16)
<223> OTHER INFORMATION: wherein Xaa is a hydrophobic amino acid
<220> FEATURE:
<221> NAME/KEY: variant
```

```
<222> LOCATION: (17)..(18)
<223> OTHER INFORMATION: wherein Xaa is any amino acid
<220> FEATURE:
<221> NAME/KEY: variant
<222> LOCATION: (19)..(19)
<223> OTHER INFORMATION: wherein Xaa is any amino acid, or is not
      present
<220> FEATURE:
<221> NAME/KEY: variant
<222> LOCATION: (20)..(20)
<223> OTHER INFORMATION: wherein Xaa is a hydrophobic amino acid
<220> FEATURE:
<221> NAME/KEY: variant
<222> LOCATION: (21)..(21)
<223> OTHER INFORMATION: wherein Xaa is a hydrophobic amino acid, or is
      not present
<220> FEATURE:
<221> NAME/KEY: variant
<222> LOCATION: (22)..(22)
<223> OTHER INFORMATION: wherein Xaa is a charged amino acid
<220> FEATURE:
<221> NAME/KEY: variant
<222> LOCATION: (23)..(24)
<223> OTHER INFORMATION: wherein Xaa is a hydrophobic amino acid
<220> FEATURE:
<221> NAME/KEY: variant
<222> LOCATION: (25)..(26)
<223> OTHER INFORMATION: wherein Xaa is any amino acid
<220> FEATURE:
<221> NAME/KEY: variant
<222> LOCATION: (27)..(28)
<223> OTHER INFORMATION: wherein Xaa is a hydrophobic amino acid

<400> SEQUENCE: 57

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa
            20                  25

<210> SEQ ID NO 58
<211> LENGTH: 23
<212> TYPE: PRT
<213> ORGANISM: Artificial
<220> FEATURE:
<223> OTHER INFORMATION: Penetrating peptide
<220> FEATURE:
<221> NAME/KEY: variant
<222> LOCATION: (1)..(3)
<223> OTHER INFORMATION: wherein Xaa is a hydrophobic amino acid
<220> FEATURE:
<221> NAME/KEY: variant
<222> LOCATION: (4)..(4)
<223> OTHER INFORMATION: wherein Xaa is a charged amino acid
<220> FEATURE:
<221> NAME/KEY: variant
<222> LOCATION: (5)..(10)
<223> OTHER INFORMATION: wherein Xaa is a hydrophobic amino acid
<220> FEATURE:
<221> NAME/KEY: variant
<222> LOCATION: (11)..(11)
<223> OTHER INFORMATION: wherein Xaa is any amino acid
<220> FEATURE:
<221> NAME/KEY: variant
<222> LOCATION: (12)..(12)
<223> OTHER INFORMATION: wherein Xaa is a hydrophobic amino acid
<220> FEATURE:
<221> NAME/KEY: variant
<222> LOCATION: (13)..(15)
<223> OTHER INFORMATION: wherein Xaa is any amino acid
<220> FEATURE:
<221> NAME/KEY: variant
<222> LOCATION: (16)..(16)
<223> OTHER INFORMATION: wherein Xaa is a hydrophobic amino acid
<220> FEATURE:
<221> NAME/KEY: variant
<222> LOCATION: (17)..(17)
```

```
<223> OTHER INFORMATION: wherein Xaa is a charged amino acid
<220> FEATURE:
<221> NAME/KEY: variant
<222> LOCATION: (18)..(19)
<223> OTHER INFORMATION: wherein Xaa is a hydrophobic amino acid
<220> FEATURE:
<221> NAME/KEY: variant
<222> LOCATION: (20)..(21)
<223> OTHER INFORMATION: wherein Xaa is any amino acid
<220> FEATURE:
<221> NAME/KEY: variant
<222> LOCATION: (22)..(23)
<223> OTHER INFORMATION: wherein Xaa is a hydrophobic amino acid

<400> SEQUENCE: 58

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 59
<211> LENGTH: 205
<212> TYPE: PRT
<213> ORGANISM: Haemophilus influenzae

<400> SEQUENCE: 59

Met Lys Asn Tyr His Asp Ile Val Leu Ala Leu Ala Gly Val Cys Gln
1               5                   10                  15

Ser Ala Lys Leu Val His Gln Leu Ala Thr Glu Ser Arg Ala Asp Ser
            20                  25                  30

Glu Thr Phe Leu Thr Ala Leu Asn Ser Leu Phe Ile Thr Gln Pro Gln
        35                  40                  45

Arg Ile Glu Asp Val Phe Gly Gly Glu Val Arg His Leu Lys Leu Gly
    50                  55                  60

Leu Glu Thr Leu Ile His Gln Leu Asn Ala Gln Gly Asp Gln Asn Leu
65                  70                  75                  80

Thr Arg Tyr Trp Leu Ser Leu Leu Ala Leu Glu Gly Lys Leu Ser Lys
                85                  90                  95

Asn Ser Asp Ala Lys Gln Thr Leu Gly Asn Arg Ile Ser Arg Leu Lys
            100                 105                 110

Glu Gln Glu Ile His Tyr Ala Arg Asp Ser Glu Thr Met Leu Ser Ile
        115                 120                 125

Met Ala Asn Ile Tyr Ser Asp Ile Ile Ser Pro Leu Gly Lys Lys Ile
    130                 135                 140

His Ile Leu Gly Ser Pro Asp Tyr Leu Arg Gln Glu Leu Val Gln Asn
145                 150                 155                 160

Lys Ile Arg Ala Val Leu Leu Ala Gly Ile Arg Ser Ala Val Leu Trp
                165                 170                 175

Lys Gln Met Gly Gly Thr Lys Trp Gln Ile Leu Phe Phe Arg Arg Lys
            180                 185                 190

Leu Leu Ala Thr Ala Lys Gln Ile Tyr Ser Ser Ile Tyr
        195                 200                 205

<210> SEQ ID NO 60
<211> LENGTH: 203
<212> TYPE: PRT
<213> ORGANISM: Pasteurella multocida

<400> SEQUENCE: 60

Met Ala Asn Tyr Tyr Asp Ile Thr Leu Ala Leu Ala Gly Val Cys Gln
1               5                   10                  15
```

-continued

```
Ala Ala Lys Leu Val Gln Gln Phe Ala His Glu Gly Gln Ala Asp Gln
            20                  25                  30

Ala Ala Phe Glu Thr Ser Leu Asn Thr Leu Leu Gln Ile Tyr Pro Glu
        35                  40                  45

Asp Thr Leu Ala Val Phe Gly Gly Lys Ala Gln Asn Leu Lys Leu Gly
    50                  55                  60

Leu Glu Thr Leu Leu Glu Gln Met His Gly Thr Gly Ser Asp Leu Ser
65                  70                  75                  80

Arg Tyr Trp Ile Ser Leu Leu Ala Leu Glu Ser Lys Leu Asn Lys Asp
                85                  90                  95

Pro His Ala Lys Ala Glu Leu Ala Arg Arg Ile Gln Tyr Leu Pro Thr
            100                 105                 110

Gln Leu Glu His Tyr Asp Leu Asp Glu Gln Met Leu Ser Thr Leu
        115                 120                 125

Ala Ser Ile Tyr Val Asp Val Ile Ser Pro Leu Gly Lys Lys Ile Gln
    130                 135                 140

Val Thr Gly Ser Thr Leu Tyr Leu Gln Gln Leu Ala Met His His Arg
145                 150                 155                 160

Ile Arg Ala Cys Leu Leu Ala Gly Ile Arg Ser Ala Val Leu Trp Arg
                165                 170                 175

Gln Val Gly Gly Thr Lys Trp Gln Val Leu Phe Ser Arg Arg Lys Ile
            180                 185                 190

Ile Ala Met Ala Lys Gln Ile Tyr Ser Ser Leu
        195                 200
```

<210> SEQ ID NO 61
<211> LENGTH: 213
<212> TYPE: PRT
<213> ORGANISM: Escherichia coli

<400> SEQUENCE: 61

```
Met Ala Lys Asn Tyr Tyr Asp Ile Thr Leu Ala Leu Ala Gly Ile Cys
1               5                   10                  15

Gln Ser Ala Arg Leu Val Gln Gln Leu Ala His Gln Gly His Cys Asp
            20                  25                  30

Ala Asp Ala Leu His Val Ser Leu Asn Ser Ile Ile Asp Met Asn Pro
        35                  40                  45

Ser Ser Thr Leu Ala Val Phe Gly Gly Ser Glu Ala Asn Leu Arg Val
    50                  55                  60

Gly Leu Glu Thr Leu Leu Gly Val Leu Asn Ala Ser Ser Arg Gln Gly
65                  70                  75                  80

Leu Asn Ala Glu Leu Thr Arg Tyr Thr Leu Ser Leu Met Val Leu Glu
                85                  90                  95

Arg Lys Leu Ser Ser Ala Lys Gly Ala Leu Asp Thr Leu Gly Asn Arg
            100                 105                 110

Ile Asn Gly Leu Gln Arg Gln Leu Glu His Phe Asp Leu Gln Ser Glu
        115                 120                 125

Thr Leu Met Ser Ala Met Ala Ile Tyr Val Asp Val Ile Ser Pro
    130                 135                 140

Leu Gly Pro Arg Ile Gln Val Thr Gly Ser Pro Ala Val Leu Gln Ser
145                 150                 155                 160

Pro Gln Val Gln Ala Lys Val Arg Ala Thr Leu Leu Ala Gly Ile Arg
                165                 170                 175

Ala Ala Val Leu Trp His Gln Val Gly Gly Gly Arg Leu Gln Leu Met
```

```
                180             185             190
Phe Ser Arg Asn Arg Leu Thr Thr Gln Ala Lys Gln Ile Leu Ala His
            195                 200                 205

Leu Thr Pro Glu Leu
    210

<210> SEQ ID NO 62
<211> LENGTH: 204
<212> TYPE: PRT
<213> ORGANISM: Vibrio cholerae

<400> SEQUENCE: 62

Met Ala Asn Ala Ile Tyr Asp Arg Thr Ile Ala Phe Ala Gly Ile Cys
1               5                   10                  15

Gln Ala Val Ala Leu Val Gln Gln Val Ala Lys Asn Gly Tyr Cys Asp
            20                  25                  30

Ser Asp Ala Phe Glu Thr Ser Leu Lys Ala Ile Thr Cys Thr Asn Pro
        35                  40                  45

Ser Asn Thr Leu Glu Val Phe Gly His Glu Ser Gln Leu Lys Leu Gly
    50                  55                  60

Leu Glu Cys Leu Val Lys Gly Ile Asp Ser Thr Pro Ser Gly Ser Glu
65                  70                  75                  80

Ile Thr Arg Tyr Leu Ile Ser Leu Met Ala Leu Glu Arg Lys Leu Ser
                85                  90                  95

Gly Arg Arg Asp Ala Met Ser Gln Leu Gly Asp Arg Ile Gln Met Ile
            100                 105                 110

Glu Arg Gln Leu Asp His Phe Asp Leu Phe Asp Asp Gln Met Ile Ser
        115                 120                 125

Asn Leu Ala Ser Ile Tyr Leu Asp Val Ile Ser Pro Ile Gly Pro Arg
    130                 135                 140

Ile Gln Val Thr Gly Thr Pro Ala Val Leu Gln Gln Thr Ala Asn Gln
145                 150                 155                 160

His Lys Val Arg Ala Leu Leu Leu Ser Gly Ile Arg Cys Ala Val Leu
                165                 170                 175

Trp Arg Gln Val Gly Gly Arg Arg His Leu Ile Phe Gly Arg Lys
            180                 185                 190

Lys Met Ile Glu Gln Ala Gln Ile Leu Leu Ala Arg
        195                 200

<210> SEQ ID NO 63
<211> LENGTH: 211
<212> TYPE: PRT
<213> ORGANISM: Buchnera aphidicola

<400> SEQUENCE: 63

Met Lys Lys Ile His Leu Ile Thr Leu Ser Leu Ala Gly Ile Cys Gln
1               5                   10                  15

Ser Ala His Leu Val Gln Gln Leu Ala Tyr Ser Gly Lys Cys Asp Ser
            20                  25                  30

Asn Ala Phe Ser Ile Cys Leu Lys Ser Ile Leu Glu Ile Asn Pro Thr
        35                  40                  45

Ser Phe Ile Ala Ile Tyr Gly Asn His Glu Lys Asn Leu Ile Ile Gly
    50                  55                  60

Leu Glu Ile Leu Leu Ser Thr Leu Thr Phe Ser Ser Phe Ser Tyr Ser
65                  70                  75                  80

Tyr Ile Glu Leu Ile Lys Tyr Ile Ser Asn Met Met Ile Ile Glu Lys
```

-continued

```
                    85                  90                  95
Lys Leu Lys Lys Ser Arg Thr Ala Ile Tyr Ser Leu Lys Asn Lys Ile
                100                 105                 110
Ser Val Ile Ser Ser Glu Tyr Tyr Leu Asn Tyr Asn Ile Lys Asn Leu
                115                 120                 125
Thr Arg Lys Leu Gly Glu Leu Tyr Leu Glu Ile Ile Ser Ser Leu Gly
            130                 135                 140
Ser Arg Ile Val Ile Lys Gly Ile Lys Asp Phe Leu Gln Asp His Gln
145                 150                 155                 160
Ile Gln Glu Lys Ile Arg Cys Leu Leu Phe Ser Gly Ile Arg Ala Ile
                165                 170                 175
Val Leu Trp Lys Gln Tyr Gly Gly Asn Gln Leu Gln Leu Ile Tyr Phe
            180                 185                 190
Arg Tyr Phe Ile Ile Lys Lys Ala Lys Lys Ile Leu Tyr His Leu Lys
        195                 200                 205
Asp Ala Thr
    210
```

<210> SEQ ID NO 64
<211> LENGTH: 206
<212> TYPE: PRT
<213> ORGANISM: Pseudomonas aeruginosa

<400> SEQUENCE: 64

```
Met Ser Asp Pro Arg Gln Gln Leu Ile Ala Leu Gly Ala Val Phe Glu
1               5                   10                  15
Ser Ala Leu Val Asp Lys Leu Ala Arg Thr Gly Gln Ile Ser Glu
            20                  25                  30
Ala Pro Leu Gly Cys Met Leu Gly Ser Leu Leu Ala Arg Asn Pro Ala
        35                  40                  45
Ser Thr Leu Asp Val Tyr Gly Gly Asp Ser Leu Asn Leu Arg Asp Gly
    50                  55                  60
Phe Lys Ala Leu Ala Ser Ala Leu Glu Arg Lys Pro Gly Ser Leu Gln
65                  70                  75                  80
Arg Glu Pro Leu Arg Tyr Ala Leu Ala Met Leu Thr Leu Glu Arg Gln
                85                  90                  95
Leu Asp Lys Arg Gly Asp Met Leu Asp Leu Ile Gly Gln Arg Leu Asp
                100                 105                 110
Gln Val Glu Gln Gln Val Gln His Phe Gly Leu Val His Glu Asn Val
            115                 120                 125
Ile Ala Ser Phe Ala Ser Ile Tyr Gln Asp Thr Leu Ser Thr Phe Arg
        130                 135                 140
Gln Arg Ile Gln Val His Gly Asp Met Arg His Leu Gln Val Ser Ser
145                 150                 155                 160
Asn Ala Ala Arg Ile Arg Ala Leu Leu Leu Ala Gly Ile Arg Ser Ala
                165                 170                 175
Arg Leu Trp Arg Gln Leu Gly Gly Ser Arg Trp Gln Met Val Phe Ser
            180                 185                 190
Arg Arg Arg Leu Leu Asn Glu Leu Tyr Pro Leu Leu Arg Gly
        195                 200                 205
```

<210> SEQ ID NO 65
<211> LENGTH: 204
<212> TYPE: PRT
<213> ORGANISM: Xylella fastidiosa -continued

```
<400> SEQUENCE: 65

Met Asn Ala Leu Ile Asp Asn Arg Val Leu Ala Leu Ala Gly Val Val
1               5                   10                  15

Gln Ala Leu Gln Gln Val Arg Gln Ile Ala Glu Thr Gly Gln Ser Glu
            20                  25                  30

Thr Ser Ala Val Arg Thr Ala Ile Asn Ser Val Leu Arg Ile Asp Ala
        35                  40                  45

Glu Ser Pro Glu Ala Val Tyr Gly Arg Ile Arg Asp Leu Thr Gln Gly
    50                  55                  60

Leu Gln Leu Leu His Asp Tyr Phe Gly Asn Gln Leu Arg Asp Gln Leu
65                  70                  75                  80

Leu Pro Arg Leu Ala Leu Ala Val Leu Gln Leu Glu Arg Arg Phe Ile
                85                  90                  95

Arg Asp Thr Ser Ile Val Ala Ala Val Ser Ala Gly Ile Thr Gln Ala
            100                 105                 110

Ala His Gln Val Glu Gln Thr Gly Asp Ser Ala His Pro Glu Val Leu
        115                 120                 125

Ser Thr Leu Gly Ala Leu Tyr Ala Asn Thr Ile Ser His Leu Arg Pro
    130                 135                 140

Arg Ile Ile Val Gln Gly Asn Pro His Tyr Leu Gly Gln Ala Gly Val
145                 150                 155                 160

Val Ala Glu Ile Arg Ala Met Leu Leu Ala Ala Leu Arg Ser Ala Val
                165                 170                 175

Leu Trp Arg Gln Leu Asn Gly Asn Leu Leu Asp Phe Met Leu Ala Lys
            180                 185                 190

Arg Ala Met Ala Ala Ala Thr Glu Arg Ala Leu Arg
        195                 200
```

AMINO ACID SEQUENCES CAPABLE OF FACILITATING PENETRATION ACROSS A BIOLOGICAL BARRIER

RELATED APPLICATIONS

This Application is a continuation-in-part of PCT/IB03/00968, filed on Feb. 7, 2003, which claims priority to U.S. Ser. No. 60/355,396, filed Feb. 7, 2002, each of which is incorporated herein by reference in its entirety.

TECHNICAL FIELD OF THE INVENTION

This invention relates to novel penetration compositions capable of facilitating penetration of an effector across biological barriers.

BACKGROUND OF THE INVENTION

Techniques enabling efficient transfer of a substance of interest across a biological barrier are of considerable interest in the field of biotechnology. For example, such techniques may be used for the transport of a variety of different substances across a biological barrier regulated by tight junctions (i.e., the mucosal epithelia, which includes the intestinal and respiratory epithelia and the vascular endothelia, which includes the blood-brain barrier).

The intestinal epithelium represents the major barrier to absorption of orally administered compounds, e.g., drugs and peptides, into the systemic circulation. This barrier is composed of a single layer of columnar epithelial cells (primarily enterocytes, goblet cells, endocrine cells, and paneth cells), which are joined at their apical surfaces by the tight junctions. See Madara et al., PHYSIOLOGY OF THE GASTROINTESTINAL TRACT; $2^{nd}$ Ed., Johnson, ed., Raven Press, New York, pp. 1251–66 (1987).

Compounds that are presented in the intestinal lumen can enter the blood stream through active or facilitative transport, passive transcellular transport, or passive paracellular transport. Active or facilitative transport occurs via cellular carriers, and is limited to transport of low molecular weight degradation products of complex molecules such as proteins and sugars, e.g., amino acids, pentoses, and hexoses. Passive transcellular transport requires partitioning of the molecule through both the apical and basolateral membranes. This process is limited to relatively small hydrophobic compounds. See Jackson, PHYSIOLOGY OF THE GASTROINTESTINAL TRACT; $2^{nd}$ Ed., Johnson, ed., Raven Press, New York, pp. 1597–1621 (1987). Consequently, with the exception of those molecules that are transported by active or facilitative mechanisms, absorption of larger, more hydrophilic molecules is, for the most part, limited to the paracellular pathway. However, the entry of molecules through the paracellular pathway is primarily restricted by the presence of the tight junctions. See Gumbiner, *Am. J. Physiol.*, 253:C749–C758 (1987); Madara, *J. Clin. Invest.*, 83:1089–94 (1989).

Therefore, large hydrophilic molecules of therapeutic value present a difficult problem in the field of drug delivery. While they are readily soluble in water, and thus easily dissolve in physiological media, such molecules are barred from absorption by the mucosal layer due to their cell-membrane impermeability. The epithelial cell membrane is composed of a phospholipid bilayer in which proteins are embedded via hydrophobic segments. Thus, the cell membrane constitutes a very strong barrier for transport of hydrophilic substances, including peptides and proteins.

A need remains for an efficient, specific, non-invasive, low-risk means for the delivery of biologically active molecules, such as polypeptides, drugs and other therapeutic agents, across various biological barriers.

SUMMARY OF THE INVENTION

The present invention provides penetration compositions containing therapeutically active cationic or anionic impermeable molecules, in order to enable their translocation across a biological barrier. The invention also relates to methods of using penetrating peptides to translocate at least one effector across a biological barrier.

Specifically, the invention involves penetration compositions having a therapeutically effective amount of an effector, a counter ion to the effector, and a penetrating peptide. Penetrating peptides have been described in WO 03/066859, (PCT/IB03/00968), filed on Feb. 7, 2003, and in U.S. Ser. No. 60/355,396, filed Feb. 7, 2002, which are incorporated herein by reference.

As used herein, a "penetration composition" includes any pharmaceutical composition that facilitates the translocation of a substance, e.g., at least one effector, across a biological barrier utilizing at least one counter ion (i.e., an anionic counter ion or a cationic counter ion) and a penetrating peptide, as described herein. Examples of biological barriers include, but are not limited to, tight junctions and the cell membrane. Moreover, those skilled in the art will recognize that translocation may occur across a biological barrier in a tissue such as epithelial cells or endothelial cells.

The invention provides penetration compositions having a pharmaceutically acceptable carrier or excipient, or a combination thereof. In various embodiments, the penetration compositions of the invention can be contained within a capsule, or can take the form of a tablet, an aqueous dispersion, suspension, or emulsion, a cream, an ointment, or a suppository. Likewise, the penetration composition can be dissolved in an at least partially water soluble solvent, such as, for example, alcohols, (e.g., n-butanol, isoamyl (=isopentyl) alchohol, iso-butanol, iso-propanol, propanol, ethanol, ter-butanol), polyols, dmf, dmso, ethers, amides, esters, or various mixtures thereof.

Penetration compositions can include a penetrating peptide coupled to at least one effector and can also include a suitable counter ion. The at least one effector can be a therapeutically active cationic or anionic impermeable molecule including, but not limited to, nucleic acids, glycosaminoglycans, proteins, peptides, or pharmaceutically active agents, such as, for example, hormones, growth factors, neurotrophic factors, anticoagulants, bioactive molecules, toxins, antibiotics, anti-fungal agents, antipathogenic agents, antigens, antibodies, antibody fragments, immunomodulators, vitamins, antineoplastic agents, enzymes, or therapeutic agents. For example, glycosaminoglycans acting as anionic impermeable compounds include, but are not limited to, heparin, heparan sulfate, chondroitin sulfate, dermatan sulfate, and hyaluronic acid. Nucleic acids serving as anionic impermeable molecules include, but are not limited to, specific DNA sequences (e.g., coding genes), specific RNA sequences (e.g., RNA aptamers, antisense RNA or a specific inhibitory RNA (RNAi)), poly CpG, or Poly I:C synthetic polymers of nucleic acids. Other suitable proteins include, but are not limited to, hormones, gonadotropins, growth factors, cytokines, neurotrophic factors, immuno-modulators, enzymes, anticoagulants, toxins, antigens, antipathogenic agents, antineoplastic agents, antibodies, antibody fragments, and other therapeutic agents. Specifically these include, but are not limited to, insulin, erythropoietin (EPO), glucagon-like peptide 1 (GLP-1), αMSH, parathyroid hormone (PTH), growth hormone, calcitonin, interleukin-2 (IL-2), α1-antitrypsin, granulocyte/monocyte colony stimulating factor (GM-CSF), granulocyte colony stimulating factor (G-CSF), T20, anti-TNF antibodies, interferon α, interferon γ, lutenizing hormone (LH), follicle-stimulating hormone (FSH), enkephalin, dalargin, kyotorphin, basic fibroblast growth factor (bFGF), hirudin, hirulog, lutenizing hormone releasing hormone (LHRH) analog, brain-derived natriuretic peptide (BNP), and neurotrophic factors.

As used herein, "cationic or anionic impermeable molecules" are molecules that are positively (cationic) or negatively (anionic) charged and are unable to efficiently cross biological barriers, such as the cell membrane or tight junctions. Preferably, cationic and anionic impermeable molecules of the invention are of a molecular weight above 200 Daltons. Anionic impermeable molecules are preferably glycosaminoglycans, nucleic acids, or net negatively charged proteins, whereas cationic impermeable molecules are preferably net positively charged proteins. A protein's net charge is determined by two factors: 1) the total count of acidic amino acids vs. basic amino acids, and 2) the specific solvent ph surroundings, which expose positive or negative residues. As used herein, "net positively or net negatively charged proteins" are proteins that, under non-denaturing pH surroundings, have a net positive or net negative electric charge. For example, interferon β is a protein that contains 23 positively charged residues (lysines and arginines), and 18 negatively charged residues (glutamic or aspartic acid residues). Therefore, under neutral or acidic pH surroundings, interferon β constitutes a net positively charged protein. Conversely, insulin is a 51 amino acid protein that contains two positively charged residues, one lysine and one arginine, and four glutamic acid residues. Therefore, under neutral or basic pH surroundings, insulin constitutes a net negatively charged protein. In general, those skilled in the art will recognize that all proteins may be considered "net negatively charged proteins", regardless of their amino acid composition, depending on their ph and/or solvent surroundings. for example, different solvents can expose negative or positive side chains depending on the solvent ph.

Penetration compositions according to the invention can also be used to enhance the penetration of smaller molecules that are otherwise impermeable through epithelial barriers. Examples of such molecules include nucleic acids (i.e., DNA, RNA, or mimetics thereof), where the counter ion is cationic. Conversely, when the counter ion is anionic, molecules such as Caspofungin, vitamin B12, and aminoglycoside antibiotics (e.g. Gentamycin, Amikacin, Tobramycin, or Neomycin) can penetrate through epithelial barriers.

Counter ions of this invention can include, for example, anionic or cationic amphipathic molecules. In one embodiment, anionic or cationic counter ions of this invention are ions that are negatively (anionic) or positively (cationic) charged and can include a hydrophobic moiety. Under appropriate conditions, anionic or cationic counter ions can establish electrostatic interactions with cationic or anionic impermeable molecules, respectively. The formation of such a complex can cause charge neutralization, thereby creating a new uncharged entity, with further hydrophobic properties due to the inherent hydrophobicity of the counter ion.

Contemplated cationic counter ions include quaternary amine derivatives, such as benzalkonium derivatives. Suitable quaternary amines can be substituted by hydrophobic residues. In general, quaternary amines contemplated by the invention have the structure: 1-R1-2-R2-3-R3-4-R4-N, wherein R1, 2, 3, or 4 are alkyl or aryl derivatives. Further, quaternary amines can be ionic liquid forming cations, such as imidazolium derivatives, pyridinium derivatives, phosphonium compounds or tetralkylammonium compounds. For example, imidazolium derivatives have the general structure of 1-R1-3-R2-imidazolium where R1 and R2 can be linear or branched alkyls with 1 to 12 carbons. Such imidazolium derivatives can be further substituted for example by halogens or an alkyl group. Specific imidazolium derivatives include, but are not limited to, 1-ethyl-3-methylimidazolium, 1-butyl-3-methylimidazolium, 1-hexyl-3-methylimidazolium, 1-methyl-3-octylimidazolium, 1-methyl-3-(3,3,4,4,5,5,6,6,7,7,8,8-tridecafluoroctyl)-imidazolium, 1,3-dimethylimidazolium, and 1,2-dimethyl-3-propylimidazolium.

Pyridinium derivatives have the general structure of 1-R1-3-R2-pyridinium where R1 is a linear or branched alkyl with 1 to 12 carbons, and R2 is H or a linear or branched alkyl with 1 to 12 carbons. Such pyridinium derivatives can be further substituted for example by halogens or an alkyl group. Pyridinium derivatives include, but are not limited to, 3-methyl-1-propylpyridinium, 1-butyl-3-methylpyridinium, and 1-butyl-4-methylpyridinium.

Suitable anionic counter ions are ions with negatively charged residues derived from strong acids such as sulfonate or phosphonate, and further contain a hydrophobic moiety. Examples of such anionic counter ions include sodium dodecyl sulphate or dioctyl sulfosuccinate.

The penetrating peptides used in penetration compositions of the invention can have at least one amino acid sequence selected from: $(BX)_4Z(BX)_2ZXB$ (SEQ ID NO:44); $ZBXB_2XBXB_2XBX_3BXB_2X_2B_2$ (SEQ ID NO:45); $ZBZX_2B_4XB_3ZXB_4$ SEQ ID NO:46); $ZB_9XBX_2B_2ZBXZBX_2$ (SEQ ID NO:47); $BZB_8XB_9X_2ZXB$ (SEQ ID NO:48); $B_2ZXZB_5XB_2XB_2X_2BZXB_2$ (SEQ ID NO:49); $XB_9XBXB_6X_3B$ (SEQ ID NO:50); $X_2B_3XB_4ZBXB_4XB_nXB$ (SEQ ID NO:51); $XB_2XZBXZB_2ZXBX_3BZXBX_3B$ (SEQ ID NO:52); $BZXBXZX_2B_4XBX_2B_2XB_4X_2$ (SEQ ID NO:53); $BZXBXZX_2B_4XBX_2B_2XB_4$ (SEQ ID NO:54); $B_2XZ_2XB_4XBX_2B_5X_2B_2$ (SEQ ID NO:55); $B^tX_tZB_mX_qB_4XBX_nB_mZB_2X_2B_2$ (SEQ ID NO:56); $B_2^tZX_3B_mX_qB_4XBX_nB_mZB_2X_2B_2$ (SEQ ID NO:57); $X_3ZB_6XBX_{NO}$ 58); and at least 12 contiguous amino acids of any of these amino acid sequences, where X is any amino acid; B is a hydrophobic amino acid; and Z is a charged amino acid; and where q is 0 or 1; m is 1 or 2; and n is 2 or 3; and where t is 1 or 2 or 3; and where the penetrating peptide is capable of translocating across a biological barrier.

Specifically, the penetrating peptide can have an amino acid sequence of any one of SEQ ID NOS: 1–15 and 24–29. In another embodiment, the invention provides a penetrating peptide having an amino acid sequence of any one of SEQ ID NOS: 22, and 30–37. In addition, the penetrating peptides of the invention include peptides having at least 12 contiguous amino acids of any of the peptides defined by SEQ ID NOS:1–15, 22, and 24–37. The penetrating peptides can be less than thirty (30), less than twenty-five (25), or less than twenty (20) amino acids in length. The invention also includes mutant or variant peptides any of whose residues may be changed from the corresponding residues shown in SEQ ID NOS: 1–15, 22, and 24–37, while still encoding a peptide that maintains its penetrating activities and physiological functions, or functional fragments thereof. For example, the fragment of an amino acid sequence of any one of SEQ ID NOS: 1–15, 22 and 24–37 is at least 10 amino acids in length, and may contain conservative or non-conservative amino acid substitutions.

In general, a penetrating peptide variant that preserves the translocating function includes any variant in which residues at a particular position in the sequence have been substituted by other amino acids, and further includes the possibility of inserting an additional residue or residues between two residues of the parent protein as well as the possibility of deleting one or more residues from the parent sequence. Any such amino acid substitution, insertion, or deletion is encompassed by the invention. In favorable circumstances, the substitution is a conservative substitution.

Amino acid substitutions at "non-essential" amino acid residues can be made in the penetrating peptides. A "non-essential" amino acid residue is a residue that can be altered from the native sequences of the penetrating peptides without altering their biological activity, whereas an "essential" amino acid residue is required for such biological activity. For example, amino acid residues that are conserved among the penetrating peptides of the invention are predicted to be particularly non-amenable to substantial alteration. Amino acids for which conservative substitutions can be made are well known within the art.

Mutations can be introduced into nucleic acids encoding penetrating peptides by standard techniques, including, but not limited to site-directed mutagenesis and PCR-mediated mutagenesis. Preferably, conservative amino acid substitutions are made at one or more predicted, non-essential amino acid residues. A "conservative amino acid substitution" is one in which the amino acid residue is replaced with an amino acid residue having a similar side chain. Families of amino acid residues having similar side chains have been defined within the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in the penetrating peptide is replaced with another amino acid residue from the same side chain family.

Alternatively, mutations can be introduced randomly along all or part of a penetrating peptide coding sequence, such as by saturation mutagenesis, and the resultant mutants can be screened for biological activity to identify mutants that retain activity. Following mutagenesis, the encoded penetrating peptide can be expressed by any recombinant technology known in the art and the activity of the protein can be determined. Amino acid substitutions can also be introduced during artificial peptide synthesis such as solid-phase synthesis of peptides.

The relatedness of amino acid families may also be determined based on side chain interactions. Substituted amino acids may be fully conserved "strong" residues or fully conserved "weak" residues. The "strong" group of conserved amino acid residues may be any one of the following groups: STA, NREQK (SEQ ID NO:17), NHQK (SEQ ID NO:18), NDEQ (SEQ ID NO:19), QHRK (SEQ ID NO:20), MILV (SEQ ID NO:21), MILF (SEQ ID NO:23), HY, FYW, wherein the single letter amino acid codes are grouped by those amino acids that may be substituted for each other. Likewise, the "weak" group of conserved residues may be any one of the following: CSA, ATV, SAG, STNK (SEQ ID NO:38), STPA (SEQ ID NO:39), SGND (SEQ ID NO:40), SNDEQK (SEQ ID NO:41), NDEQHK (SEQ ID NO:42), NEQHRK (SEQ ID NO:43), HFY, wherein the letters within each group represent the single letter amino acid code.

The penetrating peptides utilized herein are preferably modified by hydrophobic moieties. A hydrophobic agent can be a single molecule or a combination of hydrophobic molecules, like aliphatic or aromatic molecules. Examples of aliphatic hydrophobic agents include fatty acids, mono-, di-, or tri-glycerides, ethers, or cholesterol esters of fatty acids. The tri-glyceride can be tricaprin, for example. An example of an aromatic hydrophobic agent includes benzyl benzoate. The penetrating peptides are then incorporated into the construct of the penetration composition, including the desired effector. The hydrophobization of the penetrating peptide can be achieved via acylation of free amino group(s) of extra lysine(s), interspaced by glycine, alanine, or serine residues, added at the C-terminus of the penetrating peptide. Acylation of the penetrating peptide preferably utilizes long-chain fatty acids such as stearoyl, palmitoyl, oleyl, ricinoleyl, or myristoyl.

The penetrating peptides of the invention can also include amino acid analogs in which one or more peptide bonds have been replaced with an alternative type of covalent bond (a "peptide mimetic") that is not susceptible to cleavage by peptidases elaborated by the subject. Where proteolytic degradation of a peptide composition is encountered following administration to the subject, replacement of one or more particularly sensitive peptide bonds with a noncleavable peptide mimetic renders the resulting peptide derivative compound more stable, and thus, more useful as a therapeutic. Such mimetics, and methods of incorporating them into peptides, are well known in the art.

Similarly, the replacement of an L-amino acid residue by a D-amino acid residue is one standard method for rendering the compound less sensitive to enzymatic destruction. Other amino acid analogs are known in the art, such as norleucine, norvaline, homocysteine, homoserine, ethionine, and the like. Also useful is derivatizing the compound with an amino-terminal blocking group such as a t-butyloxycarbonyl, acetyl, methyl, succinyl, methoxysuccinyl, suberyl, adipyl, azelayl, dansyl, benzyloxycarbonyl, fluorenylmethoxycarbonyl, methoxyaselayl, methoxyadipyl, methoxysuberyl, and a 2,3-dinitrophenyl group.

The penetrating peptides of the invention can also be further chemically modified. For example, one or more polyethylene glycol (PEG) residues can be attached to the penetrating peptides of the invention.

The penetration composition involves the coupling of the penetrating peptide to the effector, directly or indirectly. As used herein, the term "coupled" is meant to include all such specific interactions that result in two or more molecules showing a preference for one another relative to some third molecule, including any type of interaction enabling a physical association between an effector and a penetrating peptide. Preferably this includes, but is not limited to, electrostatic interactions, hydrophobic interactions and hydrogen bonding, but does not include non-specific associations such as solvent preferences. The association must be sufficiently strong so that the effector does not dissociate before or during penetration of the biological barrier.

Furthermore, the coupling of the effector to the penetrating peptide can be achieved indirectly via a mediator. For example, such a mediator can be a large hydrophobic molecule, such as a triglyceride, that binds the effector-counter ion complex, on the one hand, and the hydrophobized penetrating peptide, on the other hand.

The invention also includes methods of producing a penetration composition by coupling a therapeutically effective amount of at least one effector with a penetrating peptide and a counter-ion to the effector. Such coupling can be via a non-covalent bond. The non-covalent bond can be achieved by adding a hydrophobic moiety to the penetrating peptide, such that the moiety enables the penetrating peptide to be incorporated at the interface of the hydrophobic vesicle in which the effector is contained.

In one embodiment, the compositions of the invention can be prepared via lyophilization of the effector (supplied under preferred pH surroundings) and the counter ion. The composition can be further supplemented by a polyanionic molecule, such as phytic acid, and/or any other constituent of the pharmaceutical excipient or carrier, which can be optionally added with the effector and counter ion during the lyophilization. The lyophilized materials can then be reconstituted under preferred solvent surroundings. During the reconstitution, other constituents, including one or more of the penetrating peptides, can be added. Other constituents can include, for example, N-methyl pirolidine, cremophore, tricaprin, pluronic F-68, aprotinin, solutol HS-15, N-acetyl Cysteine, sodium hydroxide, acetic acid, sodium acetate and/or L-Arginine.

The invention also involves methods of translocating an effector across a biological barrier by using the penetration compositions of the invention. For example, an effector can be coupled to penetration compositions according to the invention, which can then be introduced to a biological barrier, thereby effectively translocating the effector across the biological membrane.

As used herein, the term "biological barrier" is meant to include biological membranes such as the plasma membrane as well as any biological structures sealed by tight junctions (or occluding junctions) such as the mucosal epithelia, including, but not limited to, the intestinal or respiratory epithelia or the vascular endothelia, including, but not limited to, the blood-brain barrier.

The invention further includes a pharmaceutical composition containing a therapeutically or prophylactically effective amount of one or more penetrating peptides, an effector, a suitable counter ion, and additional pharmaceutically acceptable constituents. These additional constituents can assist either in the construction, solubility, or maintenance of the penetration composition. The pharmaceutical composition can further include a suitable carrier(s) and additives that protect the penetration composition such as protease inhibitors or a protection against the digestive environment of the gastrointestinal tract, such as enteric coatings. Specifically, such additional constituents include, but are not limited to, a poloxamer, N-acetyl cysteine (NAC), Aprotinin, and Solutol HS 15.

Preferred "pharmaceutical compositions" include, e.g., enteric-coated tablets and gelatin capsules comprising the active ingredient together with a) diluents, e.g., lactose, dextrose, sucrose, mannitol, sorbitol, cellulose and/or glycine; b) protease inhibitors such as Aprotinin or trasylol; c) lubricants, e.g., silica, talcum, stearic acid, its magnesium or calcium salt, poloxamer and/or polyethyleneglycol; for tablets also d) binders, e.g., magnesium aluminum silicate, starch paste, gelatin, tragacanth, methylcellulose, sodium carboxymethylcellulose and/or polyvinylpyrrolidone; e) ionic surface active agents such as poloxamer, Solutol HS15, Cremophore, and bile acids, if desired f) disintegrants, e.g., starches, agar, alginic acid or its sodium salt, or effervescent mixtures; and/or g) absorbents, colorants, flavors and sweeteners. Suppositories are advantageously prepared from fatty emulsions or suspensions. The compositions may be sterilized and/or contain adjuvants, such as preserving, reducing agents e.g., NAC (N-Acetyl-L-Cysteine), stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.01 to 75%, preferably about 0.1 to 10%, of the active ingredient.

These compositions may further contain a mixture of at least two substances selected from the group consisting of a non-ionic detergent, an ionic detergent, a protease inhibitor, and a reducing agent. For example, the non-ionic detergent may be a poloxamer or Solutol HS 15; the poloxamer may be pluronic F-68; the ionic detergent may be a bile salt; the bile salt may be Taurodeoxycholate; the protease inhibitor may be selected from the group consisting of aprotonin and soy bean trypsin inhibitor; and/or the reducing agent may be NAC.

Other suitable protease inhibitors that can be added to the penetration composition are described in Bernkop-Schnurch et al., *J. Control. Release*, 52:1–16 (1998). These include, e.g., inhibitors of luminally secreted proteases, examples of which are aprotinin, Bowman-Birk inhibitor, soybean trypsin inhibitor, chicken ovomucoid, chicken ovoinhibitor, human pancreatic trypsin inhibitor, camostate mesilate, flavonoid inhibitors, antipain, leupeptin, p-aminobenzamidine, AEBSF, TLCK, APMSF, DFP, PMSF, poly(acrylate) derivatives, chymostatin, benzyloxycarbonyl-Pro-Phe-CHO, FK-448, sugar biphenylboronic acids complexes, β-phenylpropionate, elastatinal, methoxysuccinyl-Ala-Ala-Pro-Val-chloromethylketone (MPCMK) (SEQ ID NO:66), EDTA, and chitosan-EDTA conjugates. These also include inhibitors of membrane bound proteases, such as amino acids, di- and tripeptides, amastatin, bestatin, puromycin, bacitracin, phosphinic acid dipeptide analogues, α-aminoboronic acid derivatives, Na-glycocholate, 1,10-phenantroline, acivicin, L-serine-borate, thiorphan, and phosphoramidon.

The invention also provides kits having one or more containers containing a therapeutically or prophylactically effective amount of a pharmaceutical composition or of a penetration composition of the invention.

Also described are methods of treating or preventing a disease or pathological condition by administering to a subject in which such treatment or prevention is desired, a penetration composition in an amount sufficient to treat or prevent the disease or pathological condition. For example, the disease or condition to be treated may include but are not limited to endocrine disorders, including diabetes, infertility, hormone deficiencies and osteoporosis; neurodegenerative disorders, including Alzheimer's disease and other forms of dementia, Parkinson's disease, multiple sclerosis, and Huntington's disease; cardiovascular disorders, including atherosclerosis, hyper- and hypocoagulable states, coronary disease, and cerebrovascular events; metabolic disorders, including obesity and vitamin deficiencies; renal disorders, including renal failure; haematological disorders, including anemia of different entities; immunologic and rheumatologic disorders, including autoimmune diseases, and immune deficiencies; infectious diseases, including viral, bacterial, fungal and parasitic infections; neoplastic diseases; and multi-factorial disorders, including impotence, chronic pain, depression, different fibrosis states, and short stature.

Also provided are methods of oral or nasal, i.e., mucosal, vaccination involving administering to a subject in need of vaccination an effective amount of a penetration composition of the invention, wherein the effector includes an antigen to which vaccination is desired. In one embodiment, the effector can be a protective antigen (PA) for use in a vaccine against Anthrax. In another embodiment, the effector can be a Hepatitis B surface antigen (HBs) for use in a vaccine against Hepatitis B.

The invention also includes penetrating peptides that are derived from a bacterial protein. In one embodiment, the invention provides a penetrating peptide derived from a bacterial protein having an amino acid sequence of any one of SEQ ID NOS:1–8, 10–15 and 25–29. Such a penetrating peptide can be derived from an integral membrane protein, a bacterial toxin, or an extracellular protein. The penetrating peptide can also be derived from a human neurokinin receptor. In another embodiment, the invention provides a peptide derived from a neurokinin receptor having an amino acid sequence of any one of SEQ ID NOS:9 and 24.

The details of one or more embodiments of the invention have been set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

BRIEF DESCRIPTION OF THE DRAWINGS

FIG. 1 shows amino acid sequence alignment of ORF HI0638 and its homologues from other pathogenic bacteria.

FIG. 2 shows an amino acid sequence alignment of the penetrating peptides used in this invention, as well as their organism of origin.

DETAILED DESCRIPTION OF THE INVENTION

Figure 3:
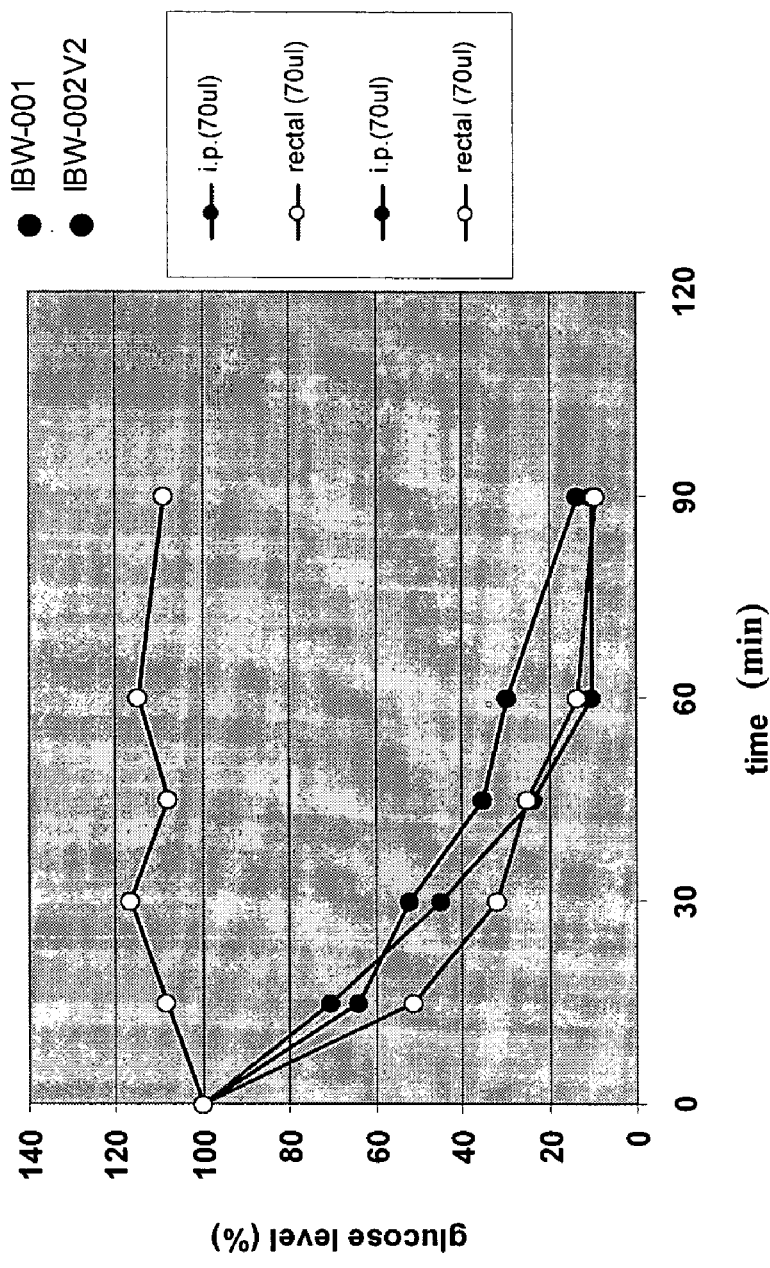
FIG. 3 shows a graph of blood glucose levels in mice plotted against time, following insulin translocation across epithelial cell membranes via administration of penetration compositions of the invention.

The use of small peptide carriers such as the penetration compositions described herein allow for high quality and purity, low immunogenicity and the potential for highly efficient delivery through biological barriers in an organism. Accordingly, peptide carriers have the potential to improve upon conventional transporters such as liposomes or viruses for the efficient delivery of many macromolecules. The present invention employs a short peptide motif to create penetration compositions to specifically transport macromolecules across biological barriers sealed by tight junctions.

The present invention provides a peptide penetration system, i.e., a penetration composition, that specifically targets various tissues, especially epithelial and endothelial ones, for the delivery of drugs and other therapeutic agents across a biological barrier. Existing transport systems known in the art are too limited to be of general application because they are inefficient, they alter the biological properties of the active substance, they kill the target cell, they irreversibly destroy the biological barrier and/or they pose too high of a risk to be used in human subjects.

The peptide penetration system of the present invention uses conserved peptide sequences from various proteins involved in paracytosis to create a penetration composition capable of crossing biological barriers. For example, a peptide encoded by or derived from ORF HI0638 of *Haemophilus influenzae* facilitates penetration of this bacterium between human lung epithelial cells without compromising the epithelial barrier. The peptide sequence encoded by ORF HI0638 is conserved in common pathogenic bacteria or symbiotic bacteria including, for example, *Haemophilus influenzae, Pasteurella multocida, Escherichia coli, Vibrio cholerae, Buchnera aphidicola, Pseudomonas aeruginosa,* and *Xylella fastidiosa.* A peptide homologous to the N-terminal sequence of HI0638 is also found in other bacteria including, for example, *Rhizobium loti, Chlamydia pneumoniae,* NprB from *Bacillus subtilis,* and pilins from *Kingella dentrificans* and *Eikenella corrodens.*

Furthermore, a similar peptide sequence is also conserved in proteins of eukaryotic origin such as the neurokinin receptor family proteins, including the human NK-1 and NK-2 receptors. It is known that the neurokinin receptor family is involved in the control of intercellular permeability including plasma extravasation and oedema formation. Extravasation, the leakage and spread of blood or fluid from vessels into the surrounding tissues, often follows inflammatory processes involved in tissue injury, allergy, burns and inflammation. In particular, when NK-1 receptors on blood vessels are activated, skin inflammation occurs due to an increase in vascular permeability. See Inoue, et al., *Inflamm. Res.,* 45:316–323 (1996). The neurokinin NK-1 receptor also mediates dural and extracranial plasma protein extravasation, thereby implicating the NK-1 receptor in the pathophysiology of migraine headache. See O'Shaughnessy and Connor, *Euro. J. of Pharm.,* 236:319–321 (1993).

The sequences of example penetrating peptides of the invention are shown in Tables 1 and 2.

TABLE 1

| Peptide/Organism | Sequence | SEQ ID NO |
|---|---|---|
| Peptide 1: from ORF HI0638 *Haemophilus influenzae* | NYHDIVLALAGVCQSAKLVHQLA | (SEQ ID NO: 1) |
| Peptide 2: from PM1850 *Pasteurella multocida* | NYYDITLALAGVCQAAKLVQQFA | (SEQ ID NO: 2) |

TABLE 1-continued

| Peptide/Organism | Sequence | SEQ ID NO |
|---|---|---|
| Peptide 3: from YCFC Escherichia coli | NYYDITLALAGICQSARLVQQLA | (SEQ ID NO: 3) |
| Peptide 4: from VC1127 Vibrio cholerae | AIYDRTIAFAGICQAVALVQQVA | (SEQ ID NO: 4) |
| Peptide 5: from BU262 Buchnera aphidicola | KIHLITLSLAGICQSAHLVQQLA | (SEQ ID NO: 5) |
| Peptide 6: from PA2627 Pseudomonas aeruginosa | DPRQQLIALGAVFESAALVDKLA | (SEQ ID NO: 6) |
| Peptide 7: from XF1439 Xylella fastidiosa | LIDNRVLALAGVVQALQQVRQIA | (SEQ ID NO: 7) |
| Peptide 8: from MLR0187 Rhizobium loti | NLPPIVLAVIGICAAVFLLQQYV | (SEQ ID NO: 8) |
| Peptide 9: from Human NK-2 Receptor | NYFIVNLALADLCMAAFNAAFNF | (SEQ ID NO: 9) |
| Peptide 10: from CPN0710/C Chlamydia pneumoniae | TAFDFNKMLDGVCTYVKGVQQYL | (SEQ ID NO: 10) |
| Peptide 11: from MLR4119 Rhizobium loti | RAILIPLALAGLCQVARAGDISS | (SEQ ID NO: 11) |
| Peptide 12: from NprB Bacillus subtilis | MRNLTKTSLLLAGLCTAAQMVFVTH | (SEQ ID NO: 12) |
| Peptide 13: from Pilin Kingella dentrificans | IELMIVIAIIGILAAIALPAYQEYV | (SEQ ID NO: 13) |
| Peptide 14: from Pilin Eikenella corrodens | IELMIVIAIIGILAAIALPAYQDYV | (SEQ ID NO: 14) |
| Peptide 15: from zonula occludens toxin (ZOT) | ASFGFCIGRLCVQDGF | (SEQ ID NO: 15) |
| Peptide 29: from Human NK-1 Receptor | NYFLVNLAFAEASMAAFNTVVNF | (SEQ ID NO: 24) |
| Peptide 30: from YCFC Escherichia coli | MNYYDITLALAGICQSARLVQQLA | (SEQ ID NO: 25) |
| Peptide 31: from YCFC Escherichia coli | MYYDITLALAGICQSARLVQQLA | (SEQ ID NO: 26) |
| Peptide 32: from YCFC Escherichia coli | MYDITLALAGICQSARLVQQLA | (SEQ ID NO: 27) |
| Peptide 33: from NprB Bacillus subtilis | MRNLTRTSLLLAGLCTAAQMVFV | (SEQ ID NO: 28) |
| Peptide 34: from ORF HI0638 Haemophilus influenzae | NYHDIVLALAGVCQSARLVHQLA | (SEQ ID NO: 29) |

The penetrating peptides of the instant invention also include peptides containing at least 12 contiguous amino acids of any of the peptides defined by SEQ ID NOS:1–15 and 24–29.

TABLE 2

| Peptide's name | SEQ ID NO. | Sequence |
|---|---|---|
| IBW-002 | 22 | AcNYYDITLALAGICQSARLVQQLAGGGKGGKNH$_2$ |
| IBW-003 | 30 | AcNLPPIVLAVIGICAAVFLLQQYVGGGKGGKNH$_2$ |
| IBW-004 | 31 | AcNYFIVNLALADLCMAAFNAAFNFGGGKGGKNH$_2$ |
| IBW-005 | 32 | AcMRNLTRTSLLLAGLCTAAQMVFVGGGKGGKNH$_2$ |
| IBW-006 | 33 | AcNYHDIVLALAGVCQSARLVHQLAGGKGGKNH$_2$ |
| IBW-007 | 34 | AcNYFLVNLAFAEASMAAFNTVVNFGGGKGGKNH$_2$ |
| IBW-002V1 | 35 | AcMNYYDITLALAGICQSARLVQQLAGGGKGGKNH$_2$ |

TABLE 2-continued

| Peptide's name | SEQ ID NO. | Sequence |
|---|---|---|
| IBW-002V2 | 36 | AcMYYDITLALAGICQSARLVQQLAGGGKGGKNH$_2$ |
| IBW-002V3 | 37 | AcMYDITLALAGICQSARLVQQLAGGGKGGKNH$_2$ |

The penetration compositions of the present invention exhibit efficient, non-invasive delivery of an unaltered biologically active substance, and thus, have many uses. For example, the penetrating peptides of the invention can be used in the treatment of bacterial infections. Since the introduction of the penicillins, pathogenic bacteria have been steadily acquiring novel mechanisms enabling a growing resistance to antibiotic therapy. The expanding number of highly insensitive bacterial pathogens presents an ever-growing challenge to physicians and caregivers. Consequently, patients are often forced to remain hospitalized for long periods, in order to receive IV antibiotic therapy, with obvious economic and medical disadvantages. Aminoglycoside antibiotics are potent antibacterial antibiotics, that are ineffectively absorbed through biological barriers. The penetration compositions of the invention can be used to deliver aminoglycosides, such as gentamycin, tobramycin, neomycin, and amikacin, across the mucosal epithelia at high yield.

Furthermore, the penetrating peptides of the invention can be used in the treatment of diabetes. Insulin levels in the blood stream must be tightly regulated. The penetration compositions of the invention can be used to deliver insulin across the mucosal epithelia at high yield. Alternative non-invasive insulin delivery methods, previously known in the art, have typical yields of 1–5% and cause intolerable fluctuations in the amount of insulin absorbed. A more innovative treatment for elevated blood glucose levels involves the use of glucagon- like peptide 1. GLP-1 is a potent hormone, which is endogenously secreted in the gastrointestinal tract upon food injection. Its important physiological action is to augment the secretion of insulin in a glucose-dependant manner, thus encompassing a novel treatment for diabetic states.

In addition, these penetration compositions also can be used to treat conditions resulting from atherosclerosis and the formation of thrombi and emboli such as myocardial infarction and cerebrovascular accidents. Specifically, the penetration compositions can be used to deliver heparin across the mucosal epithelia. Heparin is an established, effective and safe anticoagulant. However, its therapeutic use is limited by the need for parenteral administration. Thus far there has been limited success in the direction of increasing heparin absorption from the intestines, and a sustained systemic anticoagulant effect has not been achieved.

The penetration composition of this invention can also be used to treat hematological diseases and deficiency states that are amenable by administration of hematological growth factors. Erythropoietin is a glycoprotein which stimulates red blood cell production. It is produced in the kidney and stimulates the division and differentiation of committed erythroid progenitors in the bone marrow. Endogenously, hypoxia and anemia generally increase the production of erythropoietin, which in turn stimulates erythropoiesis. However, in patients with chronic renal failure (CRF), production of erythropoietin is impaired, and this erythropoietin deficiency is the primary cause of their anemia. Recombinant EPO stimulates erythropoiesis in anemic patients with CRF, including patients on dialysis as well as those who do not require regular dialysis. Additional anemia states treated by EPO include Zidovudine-treated HIV-infected patients, cancer patients on chemotherapy. Anemia in cancer patients may be related to the disease itself or the effect of concomitantly administered chemotherapeutic agents.

Another widespread cause of anemia is pernicious anemia, caused by a lack of vitamin B12. The complex mechanism of vitamin B12 absorption in the gastrointestinal tract involves the secretion and binding to Intrinsic Factor. This process is abnormal in pernicious anemia patients, resulting in lack of vitamin B12 absorption and anemia. The penetration compositions of the invention can be used to deliver vitamin B12 across the mucosal epithelia at high yield.

Colony stimulating factors are glycoproteins which act on hematopoietic cells by binding to specific cell surface receptors and stimulating proliferation, differentiation, commitment, and some end-cell functional activation. G-CSF regulates the production of neutrophils within the bone marrow and affects neutrophil progenitor proliferation, differentiation and selected end-cell functional activation, including enhanced phagocytic ability, priming of the cellular metabolism associated with respiratory burst, antibody dependent killing, and the increased expression of some functions associated with cell surface antigens.

In cancer patients, recombinant granulocyte colony-stimulating factor has been shown to be safe and effective in accelerating the recovery of neutrophil counts following a variety of chemotherapy regimens, thus preventing hazardous infectious. G-CSF can also shorten bone marrow recovery when administered after bone marrow transplantations.

The penetration composition of this invention can also be used to administer monoclonal antibodies for different indications. For example, administration of antibodies that block the signal of tumor necrosis factor (TNF) can be used to treat pathologic inflammatory processes such as rheumatoid arthritis (RA), polyarticular-course juvenile rheumatoid arthritis (JRA), and the resulting joint pathology.

Additionally, the penetration compositions of this invention can be used to treat osteoporosis. It has recently been shown that intermittent exposure to parathyroid hormone (PTH), as occurs in recombinant PTH injections, results in an anabolic response, rather than the well known catabolic reaction induced by sustained exposure to elevated PTH levels, as seen in hyperparathyroidism. Thus, non invasive administration of PTH may be beneficial for increasing bone mass in various deficiency states, like osteoporosis. See Fox, *Curr. Opin. Pharmacol.*, 2:338–344 (2002).

Currently, the delivery of effectors (e.g., the delivery of gentamycin, insulin, heparin, or erythropoietin to the blood stream) requires invasive techniques such as intravenous or intramuscular injections. One advantage of the penetration composition is that it can deliver effectors across biological barriers through non-invasive administration, including, for example oral, bucal, rectal, inhalation, insufflation, transdermal, or depository. In addition, a further advantage of the penetration composition of the invention is that it can cross the blood-brain barrier, thereby delivering effectors to the central nervous system (CNS).

The peptides described herein serve as the basis for the design of therapeutic "cargos", namely the coupling of the carriers ("penetrating peptide") with one or more therapeutic agents ("effectors"). Preferably a non-covalent bond is used to couple a penetrating peptide to one or more effectors. The penetrating peptide can be attached to a linker to which imaging compounds can be covalently attached, for example through free amino groups of lysine residues. Such a linker includes, but is not limited to, the amino acid sequence GGKGGK (SEQ ID NO:16), alternatively referred to herein as IBW-001).

A penetration composition is a composition that facilitates the passage, translocation, or penetration of a substance across a biological barrier, particularly through or between cells "sealed" by tight junctions. Translocation may be detected by any method known to those skilled in the art, including using imaging compounds, such as radioactive tagging, and/or fluorescent probes or dyes, incorporated into a penetration composition in conjunction with a paracytosis assay as described in, for example, Schilfgaarde, et al., Infect. and Immun., 68(8):4616–23 (2000). Generally, a paracytosis assay is performed by: a) incubating a cell layer with a penetration composition; b) making cross sections of the cell layers; and c) detecting the presence of the peptides or penetration compositions. The detection step may be carried out by incubating the fixed cell sections with labeled antibodies directed to the peptide, followed by detection of an immunological reaction between the peptide and the labeled antibody. Alternatively, the peptide may be labeled using a radioactive label, or a fluorescent label, or a dye in order to directly detect the presence of the peptide. Further, a bioassay can be used to monitor the peptide translocation. For example, using a bioactive molecules such as erythropoietin, included in a penetration composition, the increase in hemoglobin or hematocrit can be measured. Similarly, by using a bioactive molecule such as insulin coupled with a penetration composition, the drop in blood glucose level can be measured.

As used herein, the term "effector" refers to any cationic or anionic impermeable molecule or compound of, for example, biological, therapeutic, pharmaceutical, or diagnostic tracing. An anionic impermeable molecule can consist of nucleic acids (ribonucleic acid, deoxyribonucleic acid) from various origins, and particularly of human, viral, animal, eukaryotic or prokaryotic, plant, synthetic origin, etc. A nucleic acid of interest may be of a variety of sizes, ranging from, for example, a simple trace nucleotide to a genome fragment, or an entire genome. It may be a viral genome or a plasmid.

Alternatively, the effector of interest can be a protein, such as, for example, an enzyme, a hormone, a cytokine, an apolipoprotein, a growth factor, a bioactive molecule, an antigen, or an antibody, etc. As used herein, the term "bioactive molecule" refers to those compounds that have an effect on or elicit a response from living cells or tissues. A non-limiting example of a bioactive molecule is a protein. Other examples of the bioactive molecule include, but are not limited to, insulin, erythropoietin (EPO), glucagon-like peptide 1 (GLP-1), αMSH, parathyroid hormone (PTH), growth hormone, calcitonin, interleukin-2 (IL-2), α1-antitrypsin, granulocyte/monocyte colony stimulating factor (GM-CSF), granulocyte colony stimulating factor (G-CSF), T20, anti-TNF antibodies, interferon α, interferon β, interferon γ, lutenizing hormone (LH), follicle-stimulating hormone (FSH), enkephalin, dalargin, kyotorphin, basic fibroblast growth factor (bFGF), hirudin, hirulog, lutenizing hormone releasing hormone (LHRH) analog, brain-derived natriuretic peptide (BNP), or neurotrophic factors. The effector of interest can also be a glycosaminoglycan including, but not limited to, heparin, heparan sulfate, chondroitin sulfate, dermatan sulfate, and hyaluronic acid. The effector of interest can further be a nucleic acid such as DNA or RNA. Additionally, the effector can be a pharmaceutically active agent, such as, for example, a toxin, a therapeutic agent, or an antipathogenic agent, such as an antibiotic, an antiviral, an antifungal, or an anti-parasitic agent. The effector of interest can itself be directly active or can be activated in situ by the peptide, by a distinct substance, or by environmental conditions.

The terms "pharmaceutically active agent" and "therapeutic agent" are used herein interchangeably to refer to a chemical material or compound, which, when administered to an organism, induces a detectable pharmacologic and/or physiologic effect.

The penetration compositions according to the present invention are characterized by the fact that their penetration capacity is virtually independent of the nature of the effector that is coupled to it.

"Counter ions" according to this invention can include, for example, anionic or cationic amphipathic molecules, i.e., those having both polar and nonpolar domains, or both hydrophilic and hydrophobic properties. Anionic or cationic counter ions of this invention are ions that are negatively (anionic) or positively (cationic) charged and can include a hydrophobic moiety. Under appropriate conditions, anionic or cationic counter ions can establish electrostatic interactions with cationic or anionic impermeable molecules, respectively. The formation of such a complex can cause charge neutralization, thereby creating a new uncharged entity, with further hydrophobic properties due to the inherent hydrophobicity of the counter ion.

Suitable anionic counter ions include ions with negatively charged residues derived from strong acids such as sulfonate or phosphonate, and further contain a hydrophobic moiety. Examples of such anionic counter ions include, but are not limited to, sodium dodecyl sulphate and dioctyl sulfosuccinate.

Suitable cationic counter ions include quaternary amine derivatives, such as benzalkonium derivatives or other quaternary amines, which can be substituted by hydrophobic residues. In general, quaternary amines contemplated by the invention have the structure: 1-R1-2-R2-3-R3-4-R4-N, wherein R1, 2, 3, or 4 are alkyl or aryl derivatives. Further, quaternary amines can be ionic liquid forming cations, such as imidazolium derivatives, pyridinium derivatives, phosphonium compounds or tetralkylammonium compounds.

For example, imidazolium derivatives have the general structure of 1-R1-3-R2-imidazolium where R1 and R2 can be linear or branched alkyls with 1 to 12 carbons. Such imidazolium derivatives can be further substituted for example by halogens or an alkyl group. Specific imidazolium derivatives include, but are not limited to, 1-ethyl-3-methylimidazolium, 1-butyl-3-methylimidazolium, 1-hexyl-3-methylimidazolium, 1-methyl-3-octylimidazolium, 1-methyl-3-(3,3,4,4,5,5,6,6,7,7,8,8,8-tridecafluoroctyl)-imidazolium, 1,3-dimethylimidazolium, and 1,2-dimethyl-3-propylimidazolium.

Pyridinium derivatives have the general structure of 1-R1-3-R2-pyridinium where R1 is a linear or branched alkyl with 1 to 12 carbons, and R2 is H or a linear or branched alkyl with 1 to 12 carbons. Such pyridinium derivatives can be further substituted for example by halogens or an alkyl group. Pyridinium derivatives include, but are not limited to, 3-methyl-1-propylpyridinium, 1-butyl-3-methylpyridinium, and 1-butyl-4-methylpyridinium.

In one embodiment, the present invention relates to the use of the cationic component of ionic liquids. Unlike other ionic liquids, the salts of the cations according to the present invention are typically water soluble. For example, an anionic counterpart of the ionic liquid forming cation can be a halogen, such as chloride or bromide.

The penetration compositions of this invention involve the coupling of the penetrating peptide to the effector, directly or indirectly. As used herein, the term "coupled" is meant to include all such specific interactions that result in two or more molecules showing a preference for one another relative to some third molecule, including any type of interaction enabling a physical association between an effector and a penetrating peptide. Preferably this includes, but is not limited to, electrostatic interactions, hydrophobic interactions and hydrogen bonding, but does not include non-specific associations such as solvent preferences. The association must be sufficiently strong so that the effector does not dissociate before or during penetration of the biological barrier.

Furthermore, the coupling of the effector to the penetrating peptide can be achieved indirectly via a mediator. For example, such a mediator can be a large hydrophobic molecule, such as, for example, free fatty acids, mono-, di-, or tri-glycerides, ethers, or cholesterol esters of fatty acids, that binds the effector-counter ion complex, on the one hand, and the hydrophobized penetrating peptide, on the other hand.

Also included in the invention are methods of producing penetration compositions. For example, a penetrating peptide or effector of the penetration composition can be produced by standard recombinant DNA techniques known in the art.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Recombinant expression vectors comprise a nucleic acid in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to include promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. Expression vectors can be introduced into host cells to thereby produce proteins or peptides encoded by nucleic acids as described herein (e.g., penetrating peptides).

Recombinant expression vectors can be designed for expression of penetrating peptides or effectors of the invention in prokaryotic or eukaryotic cells. For example, penetrating peptides or effectors can be expressed in bacterial cells such as *Escherichia coli*, insect cells (using baculovirus expression vectors), yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification.

Examples of suitable inducible non-fusion *E. coli* expression vectors include pTrc (Amrann et al., (1988) *Gene* 69:301–315) and pET 11d (Studier et al., GENE EXPRESSION TECHNOLOGY: METHODS IN ENZYMOLOGY 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111–2118). Such alteration of nucleic acid sequences encoding the penetrating peptides or compositions of the invention can be carried out by standard DNA synthesis techniques.

In another embodiment, the expression vector is a yeast expression vector. Examples of vectors for expression in yeast *Saccharomyces cerivisae* include pYepSec1 (Baldari, et al., 1987. *EMBO J.* 6: 229–234), pMFa (Kurjan and Herskowitz, 1982. *Cell* 30: 933–943), pJRY88 (Schultz et al., 1987. *Gene* 54: 113–123), pYES2 (Invitrogen Corporation, San Diego, Calif.), and picZ (InVitrogen Corp, San Diego, Calif.).

Alternatively, a penetrating peptide or effectors of the invention can be expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156–2165) and the pVL series (Lucklow and Summers, 1989. *Virology* 170: 31–39).

In yet another embodiment, a nucleic acid encoding the penetrating peptides and effectors of the invention are expressed in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187–195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268–277), lymphoid-specific promoters (Calame and Eaton, 1988. *Adv. Immunol.* 43: 235–275), in particular promoters of T cell receptors (Winoto and Baltimore, 1989. *EMBO J.* 8: 729–733) and immunoglobulins (Banerji, et al., 1983. *Cell* 33: 729–740; Queen and Baltimore, 1983. *Cell* 33: 741–748), neuron-specific promoters (e.g., the neurofilament promoter; Byrne and Ruddle, 1989. *Proc. Natl. Acad. Sci. USA* 86: 5473–5477), pancreas-specific promoters (Edlund, et al., 1985. *Science* 230: 912–916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374–379) and the α-fetoprotein promoter (Campes and Tilghman, 1989. *Genes Dev.* 3: 537–546).

The invention further provides a recombinant expression vector comprising a DNA molecule encoding the penetrating peptides and effectors of the invention cloned into the expression vector in an antisense orientation. That is, the DNA molecule is operatively-linked to a regulatory sequence in a manner that allows for expression (by transcription of the DNA molecule) of an RNA molecule that is antisense to the penetrating peptide mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," *Reviews-Trends in Genetics*, Vol. 1(1) 1986.

Another aspect of the invention pertains to host cells into which a recombinant expression vector has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, the penetrating peptide or effectors can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the penetrating peptide or penetration composition, or can be introduced on a separate vector. Cells stably transfected with the introduced nucleic acid can be identified by drug selection (e.g., cells that have incorporated the selectable marker gene will survive, while the other cells die).

A host cell, such as a prokaryotic or eukaryotic host cell in culture, can be used to produce (i.e., express) a penetrating peptide or an effector of the invention. Accordingly, the invention further provides methods for producing penetrating peptides or effectors using the host cells. In one embodiment, the method comprises culturing the host cell (into which a recombinant expression vector encoding a penetrating peptide or an effector has been introduced) in a suitable medium such that the penetrating peptide or effector is produced. In another embodiment, the method further comprises isolating the penetrating peptide or penetration composition from the medium or the host cell.

The penetrating peptides and effectors of the invention can also be produced using solid-phase peptide synthesis methods known in the art. For example, a penetrating peptide can be synthesized using the Merrifield solid-phase synthesis method. (See e.g., Merrifield, R. B., *J. Am. Chem. Soc.* 85:2149 (1963); ENCYCLOPEDIA OF MOLECULAR BIOLOGY 806 (1st ed. 1994). In this method, the C-terminal amino acid is attached to an insoluble polymeric support resin (e.g., polystyrene beads), thereby forming an immobilized amino acid. To avoid unwanted reactions as the C-terminal amino acid is attached to the resin, the amino group of the C-terminal amino acid is protected or "blocked" using, for example, a tert-butyloxylcarbonyl (t-BOC) group. The blocking group, e.g., t-BOC, on the immobilized amino acid is then removed by adding a dilute acid to the solution. Before a second amino acid is attached to the immobilized peptide chain, the amino-group of the second amino acid is blocked, as described above, and the α-carboxyl group of the second amino acid is activated through a reaction with dicyclohxylcarbdiimide (DCC). The activated α-carboxyl group of the second amino acid then reacts with the free amino group of the immobilized amino acid to form a peptide bond. Additional amino acids are then individually added to the terminal amino acid of the immobilized peptide chain according to the required sequence for the desired penetrating peptide or penetration composition. Once the amino acids have been added in the required sequence, the completed peptide is released from the resin, such as for example, by using hydrogen fluoride, which does not attack the peptide bonds.

The penetrating peptides or effectors of the invention can also be synthesized using Fmoc solid-phase peptide synthesis. (See e.g., University of Illinois at Urbana-Champaign Protein Sciences Facility, *Solid-Phase Peptide Synthesis* (SPPS), at http://www.biotech.uiuc.edu/spps.htm). In this method, the C-terminal amino acid is attached to an insoluble polymeric support resin (e.g., polystyrene beads, cross-linked polystyrene resins, etc.), such as for example, via an acid labile bond with a linker molecule. To avoid unwanted reactions as the C-terminal amino acid is being attached to the resin, the amino group of the C-terminal amino acid is blocked using an Fmoc group. The blocking group, e.g., Fmoc, on the terminal amino acid of the immobilized amino acid is then removed by adding a base to the solution. Side chain functional groups are also protected using any base-stable, acid-labile groups to avoid unwanted reactions. Before the second amino acid is attached to the immobilized amino acid, the amino-group of the second amino acid is blocked, as described above, and the α-carboxyl group of each successive amino acid is activated by creating an N-hydrobenzotriazole (HOBt) ester in situ. The activated α-carboxyl group of the second amino acid and the free amino group of the immobilized amino acid then react, in the presence of a base, to form a new peptide bond. Additional amino acids are then successively added to the terminal amino acid of the immobilized peptide chain, until the desired peptide has been assembled. Once the necessary amino acids have been attached, the peptide chain can be cleaved from the resin, such as for example, by using a mixture of trifluoroacetic acid (TFA) and scavengers (e.g., phenol, thioanisol, water, ethanedithiol (EDT) and triisopropylsilan (TIS)) that are effective to neutralize any cations formed as the protecting groups attached to the side chain functional groups of the assembled peptide chain are removed.

It is well known to those skilled in the art that proteins can be further chemically modified to enhance the protein half-life in circulation. By way of non-limiting example, polyethylene glycol (PEG) residues can be attached to the penetrating peptides or effectors of the invention. Conjugating biomolecules with PEG, a process known as pegylation, is an established method for increasing the circulating half-life of proteins. Polyethylene glycols are nontoxic water-soluble polymers that, because of their large hydrodynamic volume, create a shield around the pegylated molecule, thereby protecting it from renal clearance, enzymatic degradation, as well as recognition by cells of the immune system.

Agent-specific pegylation methods have been used in recent years to produce pegylated molecules (e.g., drugs, proteins, agents, enzymes, etc.) that have biological activity that is the same as, or greater than, that of the "parent" molecule. These agents have distinct in vivo pharmacokinetic and pharmacodynamic properties, as exemplified by the self-regulated clearance of pegfilgrastim, the prolonged absorption half-life of pegylated interferon alpha-2a. Pegylated molecules have dosing schedules that are more convenient and more acceptable to patients, which can have a beneficial effect on the quality of life of patients. (See e.g., Yowell S. L. et al., Cancer Treat Rev 28 Suppl. A:3–6 (April 2002)).

The invention also includes methods of contacting biological barrier with a penetration composition in an amount sufficient to enable efficient penetration of the compositions through the barrier. The penetration composition can be provided in vitro, ex vivo, or in vivo. Furthermore, the penetration composition according to this invention may be capable of potentializing the biological activity of the coupled substance. Therefore, penetration compositions can be used to increase the biological activity of the effector.

In addition to the penetration composition, the invention also provides a pharmaceutically acceptable base or acid addition salt, hydrate, ester, solvate, prodrug, metabolite, stereoisomer, or mixture thereof. The invention also includes pharmaceutical formulations comprising a penetration composition in association with a pharmaceutically acceptable carrier, diluent, protease inhibitor, surface active agent, or excipient. A surface active agent can include, for example, poloxamers, Solutol HS15, cremophore, or bile acids/salts.

Salts encompassed within the term "pharmaceutically acceptable salts" refer to non-toxic salts of the compounds of this invention which are generally prepared by reacting the free base with a suitable organic or inorganic acid or solvent to produce "pharmaceutically-acceptable acid addition salts" of the compounds described herein. These compounds retain the biological effectiveness and properties of the free bases. Representative of such salts are the water-soluble and water-insoluble salts, such as the acetate, amsonate (4,4-diaminostilbene-2,2'-disulfonate), benzenesulfonate, benzoate, bicarbonate, bisulfate, bitartrate, borate, bromide, butyrate, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methylene-bis-2-hydroxy-3-naphthoate, embonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts.

According to the methods of the invention, a patient, i.e., a human patient, can be treated with a pharmacologically or therapeutically effective amount of a penetration composition. The term "pharmacologically or therapeutically effective amount" means that amount of a drug or pharmaceutical agent (the effector) that will elicit the biological or medical response of a tissue, system, animal or human that is being sought by a researcher or clinician.

The invention also includes pharmaceutical compositions suitable for introducing an effector of interest across a biological barrier. The compositions are preferably suitable for internal use and include an effective amount of a pharmacologically active compound of the invention, alone or in combination, with one or more pharmaceutically acceptable carriers. The compounds are especially useful in that they have very low, if any, toxicity.

Preferred pharmaceutical compositions are tablets and gelatin capsules, enteric-coated, comprising the active ingredient together with a) diluents, e.g., lactose, dextrose, sucrose, mannitol, sorbitol, cellulose and/or glycine; b) protease inhibitors including, but not limited to, aprotinin, Bowman-Birk inhibitor, soybean trypsin inhibitor, chicken ovomucoid, chicken ovoinhibitor, human pancreatic trypsin inhibitor, camostate mesilate, flavonoid inhibitors, antipain, leupeptin, p-aminobenzamidine, AEBSF, TLCK, APMSF, DFP, PMSF, poly(acrylate) derivatives, chymostatin, benzyloxycarbonyl-Pro-Phe-CHO; FK-448, sugar biphenylboronic acids complexes, β-phenylpropionate, elastatinal, methoxysuccinyl-Ala-Ala-Pro-Val-chloromethylketone (MPCMK) (SEQ ID NO:66), EDTA, chitosan-EDTA conjugates, amino acids, di-peptides, tripeptides, amastatin, bestatin, puromycin, bacitracin, phosphinic acid dipeptide analogues, α-aminoboronic acid derivatives, Na-glycocholate, 1,10-phenantroline, acivicin, L-serine-borate, thiorphan, and phosphoramidon; c) lubricants, e.g., silica, talcum, stearic acid, its magnesium or calcium salt, poloxamer and/or polyethyleneglycol; for tablets also d) binders, e.g., magnesium aluminum silicate, starch paste, gelatin, tragacanth, methylcellulose, sodium carboxymethylcellulose and/or polyvinylpyrrolidone; if desired e) disintegrants, e.g., starches, agar, alginic acid or its sodium salt, or effervescent mixtures; and/or f) absorbents, colorants, flavors and sweeteners. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.01 to 75%, preferably about 0.1 to 10%, of the active ingredient.

Administration of the active compounds and salts described herein can be via any of the accepted modes of administration for therapeutic agents. These methods include oral, bucal, anal, bronchial, nasal, transdermal, or topical administration modes. In general, those skilled in the art will recognize that other, more invasive modes of administration, can also be used. Such modes include, for example, parenteral administration, i.e., subcutaneously, intraperitoneally, by viral infection, intravascularly, intramuscularly, etc.

Depending on the intended mode of administration, the compositions may be in solid, semi-solid or liquid dosage form, such as, for example, tablets, suppositories, pills, time-release capsules, powders, liquids, suspensions, aerosol or the like, preferably in unit dosages. The compositions will include an effective amount of active compound or the pharmaceutically acceptable salt thereof, and in addition, may also include any conventional pharmaceutical excipients and other medicinal or pharmaceutical drugs or agents, carriers, adjuvants, diluents, protease inhibitors, etc., as are customarily used in the pharmaceutical sciences.

For solid compositions, excipients include pharmaceutical grades of mannitol, lactose, starch, magnesium stearate, sodium saccharin, talcum, cellulose, glucose, sucrose, magnesium carbonate, and the like may be used. The active compound defined above, may be also formulated as suppositories using for example, polyalkylene glycols, for example, propylene glycol, as the carrier.

Liquid compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the solution or suspension.

If desired, the pharmaceutical composition to be administered may also contain minor amounts of non-toxic auxiliary substances such as wetting or emulsifying agents, pH buffering agents, and other substances such as for example, sodium acetate, triethanolamine oleate, etc.

Those skilled in the art will recognize that the penetration compositions of the instant invention can also be used as an oral or nasal, i.e., mucosal, vaccine having an antigen, to which vaccination is desired, serve as the effector. Such a vaccine may include a penetration composition including a desired antigenic sequence, including, but not limited to, the protective antigen (PA) component of Anthrax or the Hepatitis B surface antigen (HBs) of Hepatitis B. This composition is then orally or nasally administered to a subject in need of vaccination.

An "antigen" is a molecule or a portion of a molecule capable of stimulating an immune response, which is additionally capable of inducing an animal or human to produce antibody capable of binding to an epitope of that antigen. An "epitope" is that portion of any molecule capable of being recognized by and bound by a major histocompatability complex ("MHC") molecule and recognized by a T cell or bound by an antibody. A typical antigen can have one or more than one epitope. The specific recognition indicates that the antigen will react, in a highly selective manner, with its corresponding MHC and T cell, or antibody and not with the multitude of other antibodies which can be evoked by other antigens.

A peptide is "immunologically reactive" with a T cell or antibody when it binds to an MHC and is recognized by a T cell or binds to an antibody due to recognition (or the precise fit) of a specific epitope contained within the peptide. Immunological reactivity can be determined by measuring T cell response in vitro or by antibody binding, more particularly by the kinetics of antibody binding, or by competition in binding using known peptides containing an epitope against which the antibody or T cell response is directed as competitors.

Techniques used to determine whether a peptide is immunologically reactive with a T cell or with an antibody are known in the art. Peptides can be screened for efficacy by in vitro and in vivo assays. Such assays employ immunization of an animal, e.g., a mouse, a rabbit or a primate, with the peptide, and evaluation of the resulting antibody titers.

Also included within the invention are vaccines that can elicit the production of ecretory antibodies (IgA) against the corresponding antigen, as such antibodies serve as the first line of defense against a variety of pathogens. Oral or nasal i.e., mucosal, vaccination, which have the advantage of being non-invasive routes of administration, are the preferred means of immunization for obtaining secretory antibodies, although those skilled in the art will recognize that the vaccination can be administered in a variety of ways, e.g., orally, topically, or parenterally, i.e., subcutaneously, intraperitoneally, by viral infection, intravascularly, etc.

The compositions of the present invention can be administered in oral dosage forms such as tablets, capsules (each including timed release and sustained release formulations), pills, powders, granules, elixirs, tinctures, suspensions, syrups and emulsions.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, may be provided in the form of scored tablets containing 0.005, 0.01, 0.025, 0.05, 0.1, 0.25, 0.5, 1.0, 2.5, 5.0, 10.0, 15.0, 25.0, 50.0, 100.0, 250.0, 500.0 or 1000.0 mg of active ingredient.

Compounds of the present invention may be administered in a single daily dose, or the total daily dosage may be administered in divided doses of two, three or four times daily. Furthermore, preferred compounds for the present invention can be administered in bucal form via topical use of suitable bucal vehicles, bronchial form via suitable aerosols or inhalants, intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would range from 0.1% to 15%, w/w or w/v.

The compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, protease inhibitors, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, poloxamer, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methylcellulose, agar, bentonite, xanthan gum and the like.

The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Any of the above pharmaceutical compositions may contain 0.01–99%, preferably 0.1–10% of the active compounds as active ingredients.

The following EXAMPLES are presented in order to more fully illustrate the preferred embodiments of the invention. These EXAMPLES should in no way be construed as limiting the scope of the invention, as defined by the appended claims.

EXAMPLES

Example 1

Utilization of the Penetration Composition to Enable the Translocation of Aminoglycoside Antibiotics Across an Epithelial Barrier SEQ ID NO: 34 (or any other sequence from SEQ ID NO:22, 30–37) is hydrophobized via acylation of the free amino groups of the two lysine residues at the C-terminus of the penetrating peptide with a fatty acid, i.e., myristoyl. Similarly, any other sequence from SEQ ID NO: 1–15, 24–29 may be also supplemented by extra lysine residues, interspaced by glycine, alanine or serine residues, added at the penetrating peptide C-terminus, and the free amino groups of such lysine residues are acylated with a fatty acid. The hydrophobized peptide is then incorporated into the penetrating composition, which further contains a lyophilizate of (1) an aminoglycoside antibiotic, i.e., gentamycin, (2) an amphipathic counter anion, such as sodium dodecyl sulfate (SDS) or dioctyl sulfosuccinate (DSS) and (3) phytic acid. Additional constituents are specified in Table 3.

TABLE 3

| Additional constituents of the penetration composition |
| --- |
| N-Methyl Pirolidone (NMP) |
| Cremophor EL |
| Tricaprine |
| Pluronic F-68 |
| Aprotinin |
| Solutol HS-15 (SHS) |
| N-Acetyl Cysteine (NAC) |

The penetration composition is then administered to test animals, i.e. mice, in two forms: rectally or by injection into an intestinal loop. The experimental procedure involves male BALB/c mice, which are deprived of food, 18 hours prior to the experiment. For intra-intestinal injection the mice are then anesthetized and a 2 cm long incision is made along the center of the abdomen, through the skin and abdominal wall. An intestine loop is gently pulled out through the incision and placed on wet gauze beside the animal. The loop remains intact through the entire procedure and is kept wet during the whole time. The tested compound is injected into the loop, using a 26 G needle. For rectal administration the the mice are anesthetized and the penetration composition is then rectally administered to the mice, 100 μl/mouse, using a plastic tip covered with a lubricant.

Penetration is assessed in two methods: (a) direct measurement of antibiotic concentrations in the blood, and (b) measurement of antibacterial activity in serum samples from treated animals.

Example 2

Utilization of the Penetration Composition to Enable the Translocation of Cationic Antifungal Agents Such as Caspofungin Across an Epithelial Barrier SEQ ID NO: 34 (or any other sequence from SEQ ID NO:22, 30–37) is hydrophobized via acylation of the free amino groups of the two lysine residues at the C-terminus of the penetrating peptide with a fatty acid, i.e., myristoyl. Similarly, any other sequence from SEQ ID NO: 1–15, 24–29 may be also be supplemented by extra lysine residues, interspaced by glycine, alanine or serine residues, added at the penetrating peptide C-terminus, and the free amino groups of such lysine residues are acylated with a fatty acid. The hydrophobized peptide is then incorporated into the penetrating composition, which further contains a lyophilizate of (1) an antifungal agent, i.e., caspofungin, (2) an amphipathic counter anion, such as sodium dodecyl sulfate (SDS) or dioctyl sulfosuccinate (DSS) and (3) phytic acid. Additional constituents are specified in Table 4.

TABLE 4

Additional constituents of the penetration composition

N-Methyl Pirolidone (NMP)
Cremophor EL
Tricaprine
Pluronic F-68
Aprotinin
Solutol HS-15 (SHS)
N-Acetyl Cysteine (NAC)

The penetration composition is then administered to test animals, i.e., mice, in two forms: rectally or by injection into an intestinal loop. The experimental procedure involves male BALB/c mice, which are deprived of food, 18 hours prior to the experiment. For intra-intestinal injection the mice are then anesthetized and a 2 cm long incision is made along the center of the abdomen, through the skin and abdominal wall. An intestine loop is gently pulled out through the incision and placed on wet gauze beside the animal. The loop remains intact through the entire procedure and is kept wet during the whole time. The tested compound is injected into the loop, using a 26 G needle. For rectal administration the mice are anesthetized and the penetration composition is then rectally administered, 100 µl/mouse, using a plastic tip covered with a lubricant.

Penetration is assessed in two methods: (a) direct measurement of caspofungin concentrations in the blood, and (b) measurement of antifungal activity in serum samples from treated animals.

Example 3

Utilization of the Penetration Composition for Mucosal Vaccination

SEQ ID NO: 34 (or any other sequence from SEQ ID NO:22, 30–37) is hydrophobized via acylation of the free amino groups of the two lysine residues at the C-terminus of the penetrating peptide with a fatty acid, i.e., myristoyl. Similarly, any other sequence from SEQ ID NO: 1–15, 24–29 may be also be supplemented by extra lysine residues, interspaced by glycine, alanine or serine residues, added at the penetrating peptide C-terminus, and the free amino groups of such lysine residues are acylated with a fatty acid. The hydrophobized peptide is then incorporated into the penetrating composition, which further contains a lyophilizate of (1) a desired antigenic sequence, e.g., the HBs antigen of Hepatitis B, (2) an amphipathic counter anion, such as sodium dodecyl sulfate (SDS) or dioctyl sulfosuccinate (DSS) and (3) phytic acid. Additional constituents are specified in Table 3. Such a pharmaceutical composition can be administered to a subject in need of vaccination.

This method allows simple and rapid vaccination of large populations in need thereof. Another advantage of this method is the production of high titers of IgA antibodies and the subsequent presence of IgA antibodies in the epithelial mucosa, which are the sites of exposure to antigens.

Efficacy of vaccination can be demonstrated by the measurement of specific antibody titers, IgA in particular, as well as the measurement of immunological response to stimulation, such as for example, via a cutaneous hypersensitivity reaction in response to subcutaneous administration of antigen.

Example 4

Utilization of the Penetration Composition to Enable the Translocation of Heparin Across an Epithelial Barrier SEQ ID NO: 36 was hydrophobized via acylation of the free amino groups of the two lysine residues at the C-terminus of the penetrating peptide with a myristoyl. Acylation with myristoyl was achieved by incubating the peptide with myristoyl chloride in a molar ratio of 1:10, under basic pH conditions in the presence of appropriate solvents (benzyl benzoate and di-methyl formamide, with 1% bicarbonate). The hydrophobized peptide was then incorporated into the penetration composition, which further contained heparin, and the counter cation 1-butyl-3-methylimidazolium chloride (BMIC). Additional components of the penetration composition are specified in Table 5.

TABLE 5

| Penetration composition for heparin translocation | |
| --- | --- |
| Hydrophobized SEQ ID NO: 36 | 7.5 μl/ml |
| Heparin | 10 mg/ml |
| 1-butyl-3-methylimidazolium chloride (BMIC) | 4% |
| N-Methyl Pirolidone (NMP) | 10% |
| Cremophor EL | 0.37% |
| Tricaprine | 0.5% |
| Pluronic F-68 | 2% |
| Aprotinin | 20 μl/ml |
| Solutol HS-15 (SHS) | 2% |
| N-Acetyl Cysteine (NAC) | 5 μgr/ml |

In Vivo Experimental Procedure:

Four male BALB/c mice, 9–10 weeks old, were deprived of food, 18 hours prior to the experiment. The mice were anesthetized by i.p. injection of 0.05 ml of a mixture of 0.15 ml xylazine+0.85 ml of ketamin. The penetration composition was then rectally administered to the mice, 100μl/mouse, using a plastic tip covered with a lubricant. Penetration was assessed via measurement of clotting time, at different time intervals after heparin administration. Five minutes post administration the tip of the tail was cut and a 50 μl blood sample was drawn into a glass capillary. The capillary was broken at different time intervals, until clot formation was observed. This was repeated at 15, 30, 60, 90, 120 and 150 minutes post administration. The animals were subsequently sacrificed.

In similar experiments, a control peptide (SEQ ID NO:16), lacking the penetrating peptide-sequence, was similarly hydrophobized and incorporated into the penetration composition of Table 5 and then rectally administered to the mice. The average clotting time measured was only slightly elongated compared to that obtained with the full conjugate of the penetrating peptide. Results are shown in Table 6.

TABLE 6

| Mouse Sample | | Clotting time, measured at follow times after injection | | | | | | |
|---|---|---|---|---|---|---|---|---|
| # | injected | 0 | 5 min | 15 min | 30 min | 60 min | 90 min | 120 min | 150 min |
| 1 | SEQ ID NO: 16 | 1' | 1' | 1' | 2' | 5' | 4' | 2' | 3' |
| 2 | SEQ ID NO: 36 | 1.5' | 1' | 1' | 1.5' | 2.5' | 5' | 3' | 4' |
| 3 | SEQ ID NO: 36 | 2.5' | 2' | 1' | 3' | 6' | 9'* | 8'* | 6' |
| 4 | SEQ ID NO: 36 | 1.5' | 1' | 1.5' | 1.5' | 8'* | 9'* | 15'* | 17'* |
| 5 | SEQ ID NO: 36 | 1' | 2' | 3' | 2' | 9'* | 7'* | 7'* | 9'* |

*indicates appearance of blood clotting, but it did not progress even after several minutes.

Clotting time values increase in relation to the amount of heparin absorbed from the intestine into the bloodstream (i.e., in an amount that correlates to the amount of heparin absorbed). Therefore, this drug delivery system will replace the use of heparin injections.

Example 5

Utilization of the Penetration Composition to Enable the Translocation of Insulin Across an Epithelial Barrier Using HMIC as the Counter Ion SEQ ID NO: 36 (also called IBW-002V2) and SEQ ID NO: 16 (also called IBW-001) were hydrophobized via acylation of the free amino groups of the two lysine residues at the C-terminus of the penetrating peptides with a myristoyl. Acylation with myristoyl was achieved by incubating the peptide with myristoyl chloride in a molar ratio of 1:10, under basic pH conditions in the presence of appropriate solvents (benzyl benzoate and di-methyl formamide, with 1% bicarbonate). The hydrophobized peptides were then incorporated into the penetration composition, which further contained insulin, and the counter cation 1-hexyl-3-methylimidazolium chloride (HMIC). Additional components of the penetration composition are specified in Table 7.

TABLE 7

Penetration composition for insulin translocation

Hydrophobized Peptide
Insulin
1-hexyl-3-methylimidazolium chloride (HMIC)
NaOH
Acetic acid TABLE 7-continued Penetration composition for insulin translocation Sodium Acetate
L-arginine
Pluronic F-68
Aprotinin
Solutol HS-15 (SHS)
N-Acetyl Cysteine (NAC)

Eight male BALB/c mice, 9–10 weeks old, were deprived of food, 18 hours prior to the experiment. The animals were divided into 4 groups. Each preparation was administered to 2 groups of mice either i.p. (70 ul/mouse, containing 0.2 IU insulin) or rectal (70 ul/mouse, containing 0.2 IU insulin). Blood glucose levels were measured at various time intervals post administration, in blood samples drawn from the tip of the tail. Glucose levels were plotted against time post insulin administration (See FIG. 3).

As can be seen in FIG. 3, after the penetrating peptide composition with IBW-002V2 was administered, glucose levels dropped gradually and significantly, in both groups, indicating insulin absorption from the intestine into the blood stream. In contrast, with the control peptide composition (IBW-001) a significant drop in glucose levels was noticed only after i.p. administration. No change in blood glucose levels was observed after rectal administration, indicating there was no insulin absorption in this group.

Blood glucose levels decrease in relation to the amount of insulin absorbed from the intestine into the bloodstream (i.e., in an amount that correlates to the amount of insulin absorbed). Thus, this drug delivery system can replace the need for insulin injections, thereby providing an efficient, safe and convenient route of administration for diabetes patients.

Example 6

Utilization of the Penetration Composition for Mucosal Vaccination

SEQ ID NO: 34 (or any other sequence from SEQ ID NO:22, 30–37) is hydrophobized via acylation of the free amino groups of the two lysine residues at the C-terminus of the penetrating peptide with a fatty acid, i.e., myristoyl. Similarly, any other sequence from SEQ ID NO: 1–15, 24–29 may also be supplemented by extra lysine residues, interspaced by glycine, alanine or serine residues, added at the penetrating peptide C-terminus, and the free amino groups of such lysine residues are acylated with a fatty acid. The hydrophobized peptide is then incorporated into the penetrating composition, which further contains a lyophilizate of (1) a desired antigenic sequence, e.g., the PA antigen of Anthrax, (2) an amphipathic counter cation, such as 1-butyl-3-methylimidazolium chloride (BMIC) or 1-hexyl-3-methylimidazolium chloride (HMIC) and (3) phytic acid. Additional constituents are specified in Table 5. Such a pharmaceutical composition can be administered to a subject in need of vaccination.

This method allows simple and rapid vaccination of large populations in need thereof. Another advantage of this method is the production of high titers of IgA antibodies and the subsequent presence of IgA antibodies in the epithelial mucosa, which are the sites of exposure to antigens.

Efficacy of vaccination can be demonstrated by the measurement of specific antibody titers, IgA in particular, as well as the measurement of immunological response to stimulation, such as for example, via a cutaneous hypersensitivity reaction in response to subcutaneous administration of antigen.

Example 7

Utilization of the Penetration Composition to Enable The Translocation of Insulin Across an Epithelial Barrier Using BKC as the Counter Ion SEQ ID NO: 36 (also called IBW-002V2) was hydrophobized via acylation of the free amino groups of the two lysine residues at the C-terminus of the penetrating peptide with a myristoyl. Acylation with myristoyl was achieved by incubating the peptide with myristoyl chloride in a molar ratio of 1:10, under basic pH conditions in the presence of appropriate solvents (benzyl benzoate and di-methyl formamide, with 1% bicarbonate). The hydrophobized peptide was then incorporated into the penetration composition, which further contained a lyophilizate of (1) insulin, (2) the counter cation Benzalkonium Chloride (BKC), and (3) phytic acid at a ratio of 1:0.5:0.5. Additional components of the penetration composition are specified in Table 8.

TABLE 8

| Penetration composition for insulin translocation |
|---|
| Hydrophobized Peptide |
| Human Insulin |
| Benzalkonium Chloride (BKC) |
| Phytic Acid |
| NaOH |
| Acetic acid |
| Sodium Acetate |
| L-arginine |
| Pluronic F-68 |
| Aprotinin |
| Solutol HS-15 (SHS) |
| N-Acetyl Cysteine (NAC) |
| Tricaprine |
| Ethanol |

Twelve male SD rats, 160–190 gr, were deprived of food, 18 hours prior to the experiment. The animals were divided into groups. The preparations were administered as follows: Rats #1,2-rectal PBS 200 ul, rats #3,4-rectal 200 ul penetration composition as specified above without peptide (5 IU insulin), rat #5-i.p. 200 ul penetration composition with peptide (1 IU insulin), rats #6,7-rectal 200 ul penetration composition with peptide (5 IU insulin). Blood glucose levels were measured at various time intervals post administration, in blood samples drawn from the tip of the tail. Glucose levels were plotted against time post insulin administration (See FIG. 4).

TABLE 9

| | glucose (mg/dL), time post administration | | | | | |
|---|---|---|---|---|---|---|
| | 0 | 15 | 30 | 45 | 60 | 90 |
| rat # 1 | 79 | 98 | 85 | 80 | 74 | 70 |
| rat # 2 | 58 | 93 | 91 | 80 | 72 | 69 |
| rat # 3 | 83 | 67 | 80 | 77 | 72 | 72 |
| rat # 4 | 106 | 110 | 107 | 99 | 105 | 93 |
| rat # 5 | 80 | 77 | 50 | 33 | 10 | 10 |
| rat # 6 | 85 | 79 | 55 | 35 | 21 | 33 |
| rat # 7 | 93 | 78 | 53 | 39 | 23 | 31 |

10 = low

Figure 4:
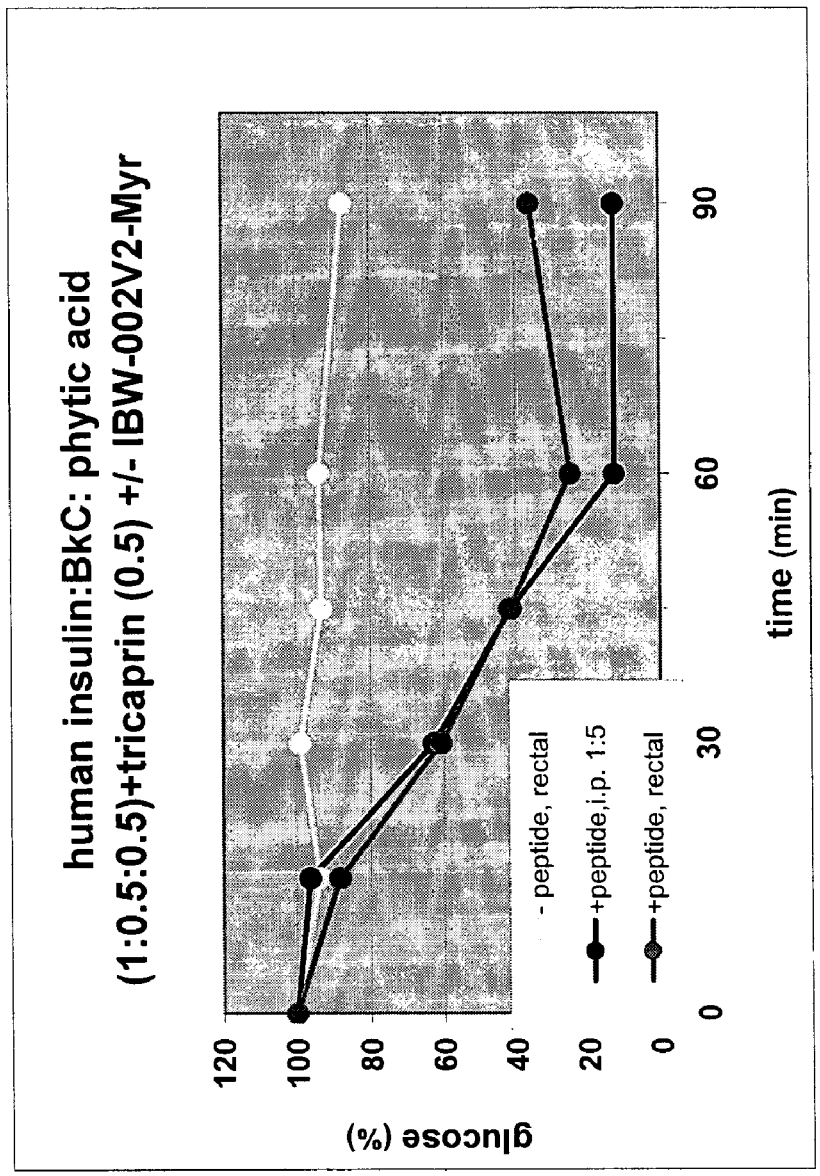
FIG. 4 shows a graph of blood glucose levels in rats plotted against time, following insulin translocation across epithelial cell membranes via administration of penetration compositions of the invention.

As can be seen in FIG. 4, after the penetrating peptide composition with IBW-002V2 was rectally administered, glucose levels dropped gradually and significantly, in both rats, indicating insulin absorption from the intestine into the blood stream. In contrast, without the peptide a significant drop in glucose levels was noticed only after i.p. administration. No change in blood glucose levels was observed after rectal administration, indicating there was no insulin absorption in these rats.

Blood glucose levels decrease in relation to the amount of insulin absorbed from the intestine into the bloodstream (i.e., in an amount that correlates to the amount of insulin absorbed). Thus, this drug delivery system can replace the need for insulin injections, thereby providing an efficient, safe and convenient route of administration for diabetes patients.

OTHER EMBODIMENTS

From the foregoing detailed description of the specific embodiments of the invention, it should be apparent that unique methods of translocation across epithelial and endothelial barriers have been described. Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims. For instance, the choice of the particular type of tissue, or the particular effector to be translocated is believed to be a matter of routine for a person of ordinary skill in the art with knowledge of the embodiments described herein.

We claim:

1. A penetration composition for non-invasive translocation of at least one effector across a biological barrier, said composition comprising:

(a) a therapeutically effective amount of said effector;

(b) a counter ion to the effector; and (c) a penetrating peptide consisting of the amino acid sequence of SEQ ID NO:24, wherein said penetrating peptide is hydrophobized.

2. The penetration composition of claim 1 further comprising a pharmaceutically acceptable excipient, pharmaceutically acceptable carrier, or a combination thereof.

3. The penetration composition of claim 1, wherein said composition is contained within a capsule.

4. The penetration composition of claim 1, wherein said composition is in the form of a tablet.

5. The penetration composition of claim 1, wherein said composition is enteric-coated.

6. The penetration composition of claim 1, wherein said composition is in the form selected from the group consisting of an aqueous dispersion, a suspension and an emulsion.

7. The penetration composition of claim 1, wherein said composition is in the form of a cream.

8. The penetration composition of claim 1, wherein said composition is in the form of an ointment.

9. The penetration composition of claim 1, wherein said composition is in the form of a suppository.

10. The penetration composition of claim 1, wherein said at least one effector is an impermeable molecule.

11. The penetration composition of claim 10, wherein said impermeable molecule is a bioactive molecule used to treat a metabolic disorder.

12. The penetration composition of claim 11, wherein said bioactive molecule is insulin.

13. The penetration composition of claim 1, wherein said counter ion is a cationic amphipathic molecule.

14. The penetration composition of claim 13, wherein said cationic amphipathic molecule is a quaternary amine comprising a hydrophobic moiety.

15. The penetration composition of claim 14, wherein said quaternary amine has the general structure of:

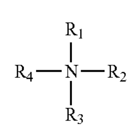

wherein R1, R2, R3 and R4 are alkyl or aryl residues.

16. The penetration composition of claim 15, wherein said quaternary amine is a benzalkonium derivative.

17. The penetration composition of claim 1, wherein said composition further comprises a polyanionic molecule.

18. The penetration composition of claim 17, wherein said polyanionic molecule is phytic acid.

19. The penetration composition of claim 1, further comprising a surface active agent.

20. The penetration composition of claim 19, wherein said surface active agent is selected from the group consisting of a poloxamer, Solutol HS15, Cremophore and bile acids.

21. The penetration composition of claim 1, wherein said composition is dissolved in an at least partially water soluble solvent.

22. The penetration composition of claim 21, wherein said at least partially water soluble solvent is selected from the group consisting of: n-butanol; isoamyl (=isopentyl) alchohol; iso-butanol; iso-propanol; propanol; ethanol; ter-butanol alcohols; polyols; DMF; DMSO; ethers; amides; esters; and mixtures thereof.

23. The penetration composition of claim 1, wherein any one or more of the components of the composition is lyophilized.

24. The penetration composition of claim 1, wherein said peptide is hydrophobized with at least one aliphatic hydrophobic molecule.

25. The penetration composition of claim 24, wherein said at least one aliphatic hydrophobic molecule is a fatty acid.

26. The penetration composition of claim 1, further comprising at least one protective agent.

27. The penetration composition of claim 26, wherein said protective agent is aprotinin.

28. The composition of claim 2, wherein the composition further comprises a non-ionic detergent.

29. The composition of claim 28, wherein the non-ionic detergent is a poloxamer or Solutol HS15.

30. The composition of claim 29, wherein the poloxamer is pluronic F-68.

31. A kit for treating diabetes comprising, in one or more containers, a therapeutically effective amount of the composition of claim 12, and a pharmaceutically acceptable carrier.

32. An isolated peptide consisting of the amino acid sequence of SEQ ID NO:24, wherein said peptide is derived from a human neurokinin receptor, and wherein said peptide is characterized by the ability to penetrate biological barriers in vivo.

33. The penetration composition of claim 1, wherein said penetrating peptide further comprises a chemical modification.

34. The penetration composition of claim 33, wherein the chemical modification comprises the attachment of one or more polyethylene glycol residues to the penetrating peptide.

35. The penetration composition of claim 1, wherein the penetrating peptide is further modified via one or more peptidic bonds, thereby protecting the peptide from gastrointestinal proteolysis.

36. The penetration composition of claim 1, wherein the penetrating peptide further comprises lysine residues interspaced by glycine, alanine, or serine residues added at the C-terminus of said penetrating peptide, and wherein the free amino groups of said lysine residues are acylated.

37. The penetration composition of claim 36, wherein acylation is achieved using a long-chain fatty acid.

38. The penetration composition of claim 37, wherein said long-chain fatty acid is selected from the group consisting of: stearoyl, palmitoyl, oleyl, ricinoleyl, lauroyl, and myristoyl.

39. The penetration composition of claim 37 further comprising N-acetyl cysteine.

40. The penetration composition of claim 39 further comprising tricaprine.

* * * * *

UNITED STATES PATENT AND TRADEMARK OFFICE
CERTIFICATE OF CORRECTION

PATENT NO. : 7,115,707 B2 Page 1 of 1
APPLICATION NO. : 10/665184
DATED : October 3, 2006
INVENTOR(S) : Ben-Sasson et al.

It is certified that error appears in the above-identified patent and that said Letters Patent is hereby corrected as shown below:

Column 87, line 17 "peptide is hydrophobized with at least one aliphatic hydro-"

should read:

--penetrating peptide is hydrophobized with at least one aliphatic hydro- --

Signed and Sealed this

Twenty-sixth Day of December, 2006

JON W. DUDAS
*Director of the United States Patent and Trademark Office*